United States Patent
Callaway et al.

(10) Patent No.: US 8,894,561 B2
(45) Date of Patent: Nov. 25, 2014

(54) MODULAR IMPLANTABLE MEDICAL PUMP

(71) Applicant: Thoratec Corporation, Pleasanton, CA (US)

(72) Inventors: Justin Aron Callaway, Goffstown, NH (US); Peter Soderholm, Tewksbury, MA (US)

(73) Assignee: Thoratec Corporation, Pleasanton, CA (US)

( * ) Notice: Subject to any disclaimer, the term of this patent is extended or adjusted under 35 U.S.C. 154(b) by 0 days.

(21) Appl. No.: 13/786,336

(22) Filed: Mar. 5, 2013

(65) Prior Publication Data
US 2013/0261375 A1    Oct. 3, 2013

Related U.S. Application Data

(60) Provisional application No. 61/606,767, filed on Mar. 5, 2012.

(51) Int. Cl.
*A61M 1/10* (2006.01)
*A61M 5/168* (2006.01)
*A61M 1/12* (2006.01)

(52) U.S. Cl.
CPC .............. *A61M 1/101* (2013.01); *A61M 1/1008* (2014.02); *A61M 5/168* (2013.01); *A61M 1/122* (2014.02)
USPC .......................................................... 600/16

(58) Field of Classification Search
None
See application file for complete search history.

(56) References Cited

U.S. PATENT DOCUMENTS

| | | | |
|---|---|---|---|
| 4,082,376 A | 4/1978 | Wehde et al. | |
| 4,458,366 A | 7/1984 | MacGregor | |
| 4,625,712 A | 12/1986 | Wampler | |
| 4,688,998 A | 8/1987 | Olsen et al. | |
| 4,704,121 A | 11/1987 | Moise | |
| 4,779,614 A | 10/1988 | Moise | |
| 4,817,586 A | 4/1989 | Wampler | |
| 4,846,152 A | 7/1989 | Wampler et al. | |
| 4,895,557 A | 1/1990 | Moise et al. | |

(Continued)

FOREIGN PATENT DOCUMENTS

| | | |
|---|---|---|
| CA | 2624704 | 4/2007 |
| CN | 101282748 | 10/2008 |

(Continued)

OTHER PUBLICATIONS

PCT Notification of Transmittal of the International Search Report and the Written Opinion for International Application No. PCT/US2013/029208, dated Jun. 24, 2013, 24 pages.

(Continued)

*Primary Examiner* — Brian T Gedeon
(74) *Attorney, Agent, or Firm* — Kilpatrick Townsend & Stockton LLP; Kenneth R. Shurtz, Esq.

(57) ABSTRACT

An implantable medical pump system can include a blood pump comprising a pump housing defining a passage therethrough and a rotor within the passage. The blood pump further includes one or more elements at least partially contained within the housing adapted to actuate the rotor to drive fluid though the passage. The pump housing includes at least one coupling feature. The system further includes an inflow cannula defining a lumen therethrough. The inflow cannula is adapted to be mechanically coupled to the at least one coupling feature.

20 Claims, 25 Drawing Sheets

(56) References Cited

U.S. PATENT DOCUMENTS

| | | | |
|---|---|---|---|
| 4,906,229 A | 3/1990 | Wampler | |
| 4,908,012 A | 3/1990 | Moise et al. | |
| 4,944,722 A | 7/1990 | Carriker et al. | |
| 4,957,504 A | 9/1990 | Chardack | |
| 4,994,078 A | 2/1991 | Jarvik | |
| 5,106,273 A | 4/1992 | Lemarquand et al. | |
| 5,385,581 A | 1/1995 | Bramm et al. | |
| 5,393,207 A | 2/1995 | Maher et al. | |
| 5,443,503 A | 8/1995 | Yamane | |
| 5,588,812 A | 12/1996 | Taylor et al. | |
| 5,613,935 A * | 3/1997 | Jarvik | 600/16 |
| 5,695,471 A | 12/1997 | Wampler | |
| 5,707,218 A | 1/1998 | Maher et al. | |
| 5,749,855 A | 5/1998 | Reitan | |
| 5,824,070 A | 10/1998 | Jarvik | |
| 5,888,242 A | 3/1999 | Antaki et al. | |
| 5,917,297 A | 6/1999 | Gerster et al. | |
| 5,928,131 A | 7/1999 | Prem | |
| 5,951,263 A | 9/1999 | Taylor et al. | |
| 6,018,208 A | 1/2000 | Maher et al. | |
| 6,050,975 A * | 4/2000 | Poirier | 604/131 |
| 6,066,086 A | 5/2000 | Antaki et al. | |
| 6,123,659 A | 9/2000 | le Blanc et al. | |
| 6,135,710 A | 10/2000 | Araki et al. | |
| 6,149,683 A | 11/2000 | Lancisi et al. | |
| 6,186,665 B1 | 2/2001 | Maher et al. | |
| 6,227,797 B1 | 5/2001 | Watterson et al. | |
| 6,227,820 B1 | 5/2001 | Jarvik | |
| 6,234,772 B1 | 5/2001 | Wampler et al. | |
| 6,278,251 B1 | 8/2001 | Schöb | |
| 6,293,901 B1 | 9/2001 | Prem | |
| 6,394,769 B1 | 5/2002 | Bearnson et al. | |
| 6,447,266 B2 | 9/2002 | Antaki et al. | |
| 6,623,475 B1 | 9/2003 | Siess | |
| 6,688,861 B2 | 2/2004 | Wampler | |
| 6,692,318 B2 | 2/2004 | McBride | |
| 6,991,595 B2 | 1/2006 | Burke et al. | |
| 7,070,398 B2 | 7/2006 | Olsen et al. | |
| 7,229,258 B2 | 6/2007 | Wood et al. | |
| 7,338,521 B2 | 3/2008 | Antaki et al. | |
| 7,563,225 B2 | 7/2009 | Sugiura | |
| 7,575,423 B2 | 8/2009 | Wampler | |
| 7,578,782 B2 | 8/2009 | Miles et al. | |
| 7,682,301 B2 | 3/2010 | Wampler et al. | |
| 7,699,586 B2 | 4/2010 | LaRose et al. | |
| 7,699,588 B2 | 4/2010 | Mendler | |
| 7,753,645 B2 | 7/2010 | Wampler et al. | |
| 7,798,952 B2 | 9/2010 | Tansley et al. | |
| 7,802,966 B2 | 9/2010 | Wampler et al. | |
| 7,824,358 B2 | 11/2010 | Cotter et al. | |
| 7,841,976 B2 | 11/2010 | McBride et al. | |
| 7,850,594 B2 | 12/2010 | Sutton et al. | |
| 7,861,582 B2 | 1/2011 | Miyakoshi et al. | |
| 7,862,501 B2 | 1/2011 | Woodard | |
| 7,927,068 B2 | 4/2011 | McBride et al. | |
| 7,959,551 B2 | 6/2011 | Jarvik | |
| 7,963,905 B2 | 6/2011 | Salmonsen et al. | |
| 7,976,271 B2 | 7/2011 | LaRose et al. | |
| 7,988,728 B2 | 8/2011 | Ayre | |
| 7,993,260 B2 | 8/2011 | Bolling | |
| 8,002,518 B2 | 8/2011 | Woodard et al. | |
| 8,096,935 B2 | 1/2012 | Sutton et al. | |
| 8,118,723 B2 | 2/2012 | Richardson et al. | |
| 8,118,724 B2 | 2/2012 | Wampler et al. | |
| 8,152,845 B2 | 4/2012 | Bourque | |
| 8,177,703 B2 | 5/2012 | Smith et al. | |
| 8,282,359 B2 | 10/2012 | Ayre et al. | |
| 8,343,028 B2 | 1/2013 | Gregoric et al. | |
| 8,353,686 B2 | 1/2013 | Cook | |
| 8,366,381 B2 | 2/2013 | Woodard et al. | |
| 8,366,599 B2 | 2/2013 | Tansley et al. | |
| 8,376,707 B2 | 2/2013 | McBride et al. | |
| 2002/0147495 A1 | 10/2002 | Petroff | |
| 2003/0100816 A1 | 5/2003 | Siess | |
| 2004/0236420 A1 | 11/2004 | Yamane et al. | |
| 2005/0004421 A1 | 1/2005 | Pacella et al. | |
| 2005/0095151 A1 | 5/2005 | Wampler et al. | |
| 2005/0107657 A1 | 5/2005 | Carrier et al. | |
| 2005/0147512 A1 | 7/2005 | Chen et al. | |
| 2005/0254976 A1 | 11/2005 | Carrier et al. | |
| 2007/0078293 A1 | 4/2007 | Shambaugh et al. | |
| 2007/0156006 A1 | 7/2007 | Smith et al. | |
| 2008/0269880 A1 | 10/2008 | Jarvik | |
| 2009/0118567 A1 | 5/2009 | Siess | |
| 2010/0069847 A1 | 3/2010 | LaRose et al. | |
| 2010/0145133 A1 | 6/2010 | Bolling | |
| 2010/0150749 A1 | 6/2010 | Horvath | |
| 2010/0152526 A1 | 6/2010 | Pacella et al. | |
| 2011/0054239 A1 | 3/2011 | Sutton et al. | |
| 2011/0144413 A1 | 6/2011 | Foster | |
| 2011/0245582 A1 | 10/2011 | Zafirelis et al. | |
| 2012/0035411 A1 | 2/2012 | LaRose et al. | |
| 2012/0046514 A1 | 2/2012 | Bourque | |
| 2012/0134793 A1 | 5/2012 | Wu et al. | |
| 2012/0134832 A1 | 5/2012 | Wu | |
| 2012/0253103 A1 | 10/2012 | Robert | |
| 2012/0310036 A1 | 12/2012 | Peters et al. | |

FOREIGN PATENT DOCUMENTS

| | | |
|---|---|---|
| DE | 19854724 A1 | 5/1999 |
| EP | 0150320 A1 | 8/1985 |
| JP | 2009111802 | 3/2009 |
| KR | 2008056754 | 6/2008 |
| WO | WO0043054 A2 | 7/2000 |
| WO | WO2005/051838 | 6/2005 |
| WO | WO2007/040663 A1 | 4/2007 |
| WO | WO2008/152425 | 12/2008 |
| WO | WO2011/081629 | 7/2011 |

OTHER PUBLICATIONS

PCT Invitation to Pay Additional Fees for Application No. PCT/US2011/056217 dated Jan. 25, 2012, 5 pages.

PCT Notification of Transmittal of the International Search Report and the Written Opinion for Application No. PCT/US2011/056217 dated May 31, 2012, 19 pages.

PCT Notification of Transmittal of the International Search Report and the Written Opinion for International Application No. PCT/US2012/060071 dated Mar. 27, 2013, 14 pages.

PCT International Preliminary Report on Patentability for Application No. PCT/US2011/056217 dated Apr. 16, 2013, 13 pages.

U.S. Final Office Action for U.S. Appl. No. 13/273,185 dated Jun. 25, 2013, 16 pages.

U.S. Non-Final Office Action for U.S. Appl. No. 13/273,185 dated Dec. 7, 2012, 17 pages.

* cited by examiner

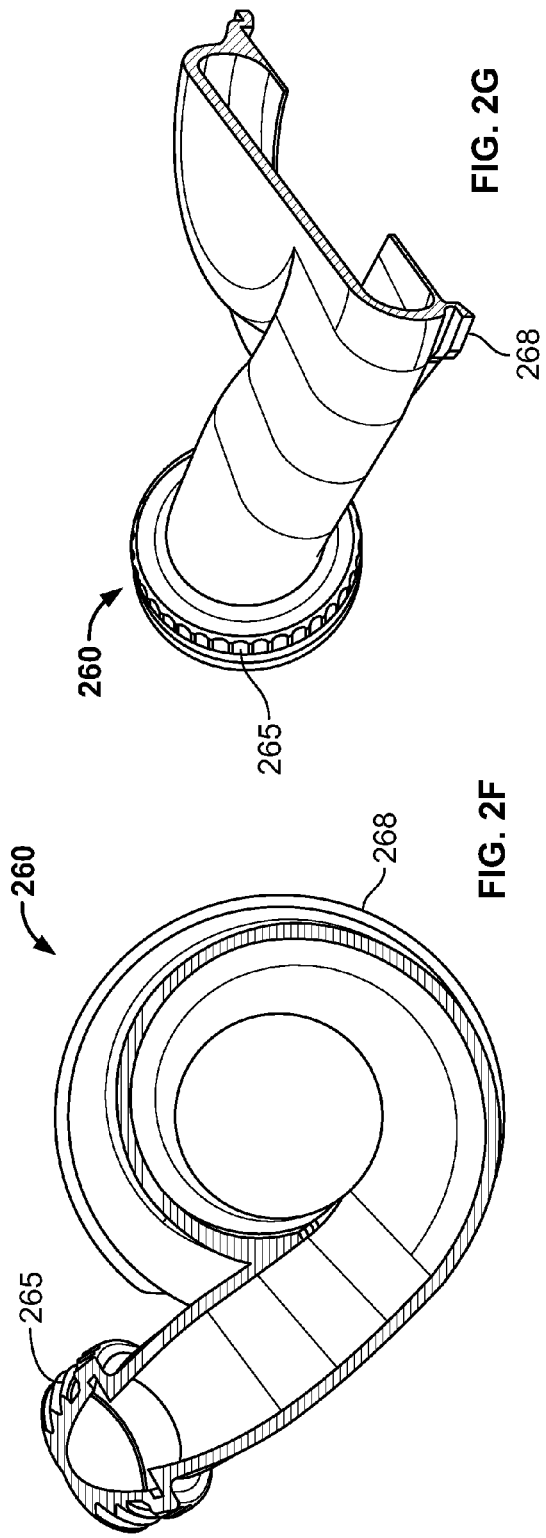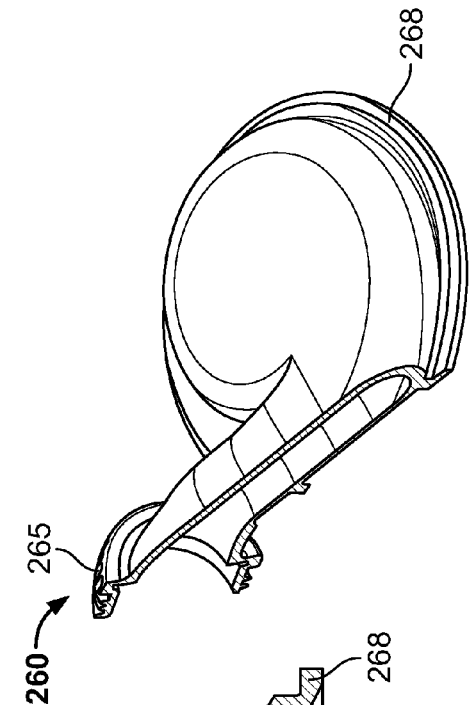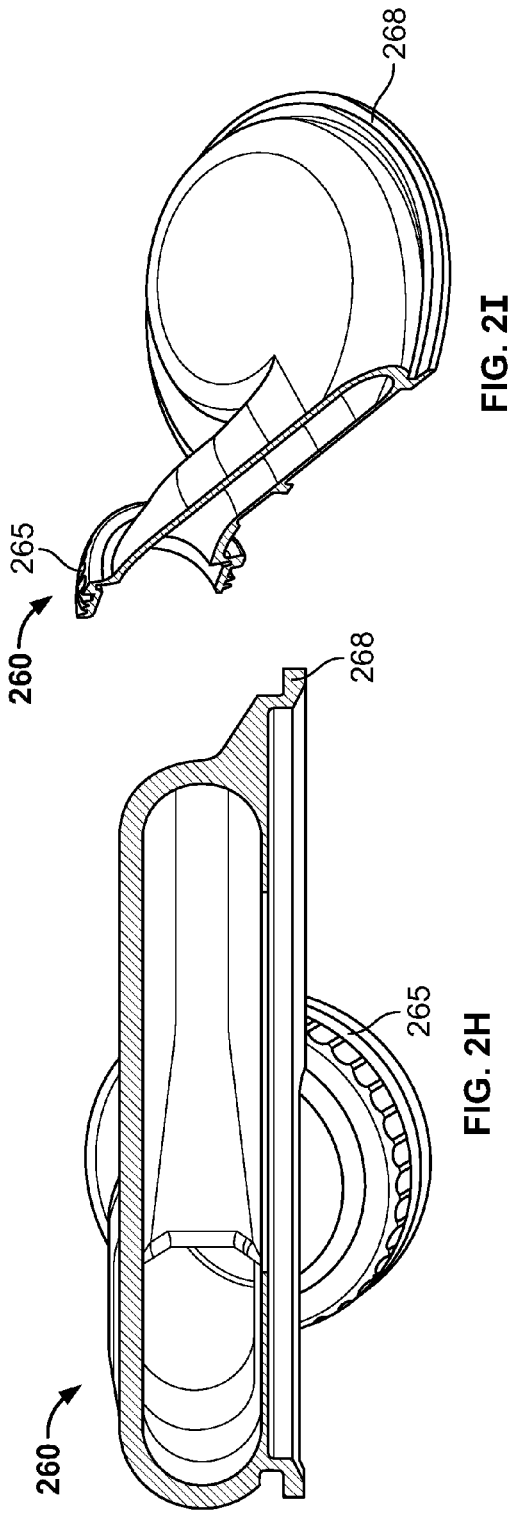

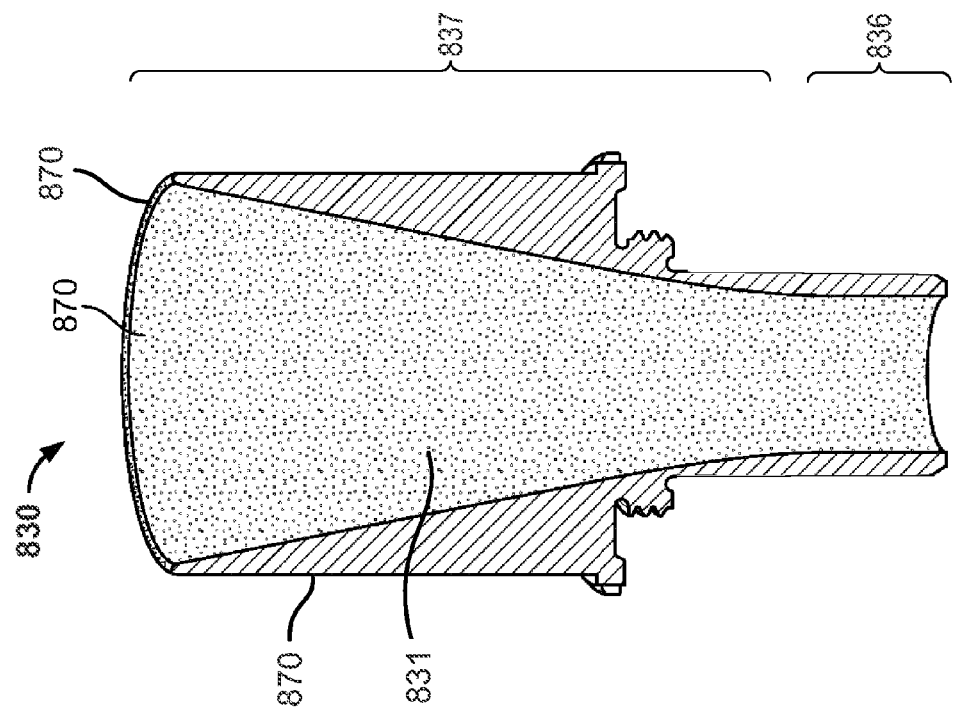
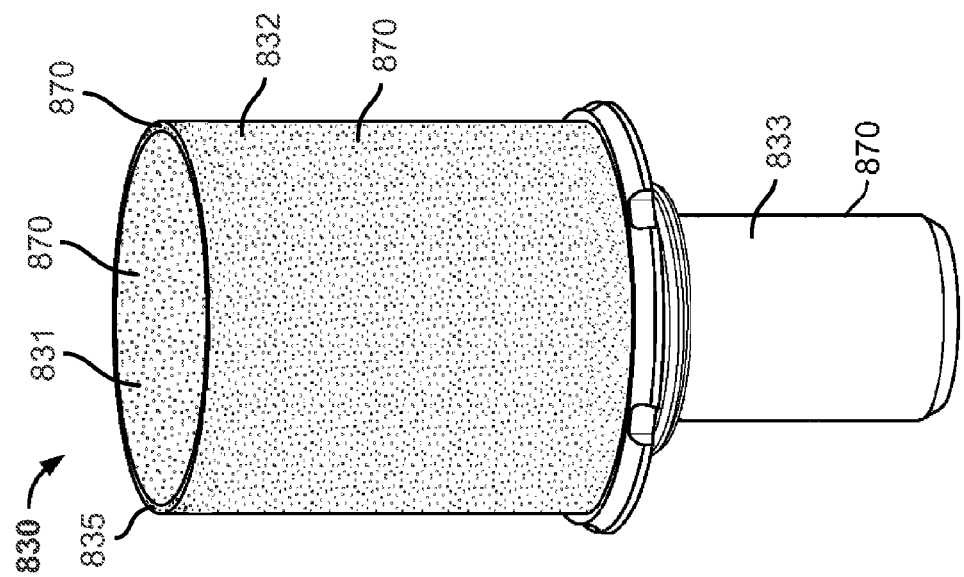
FIG. 8C
FIG. 8B

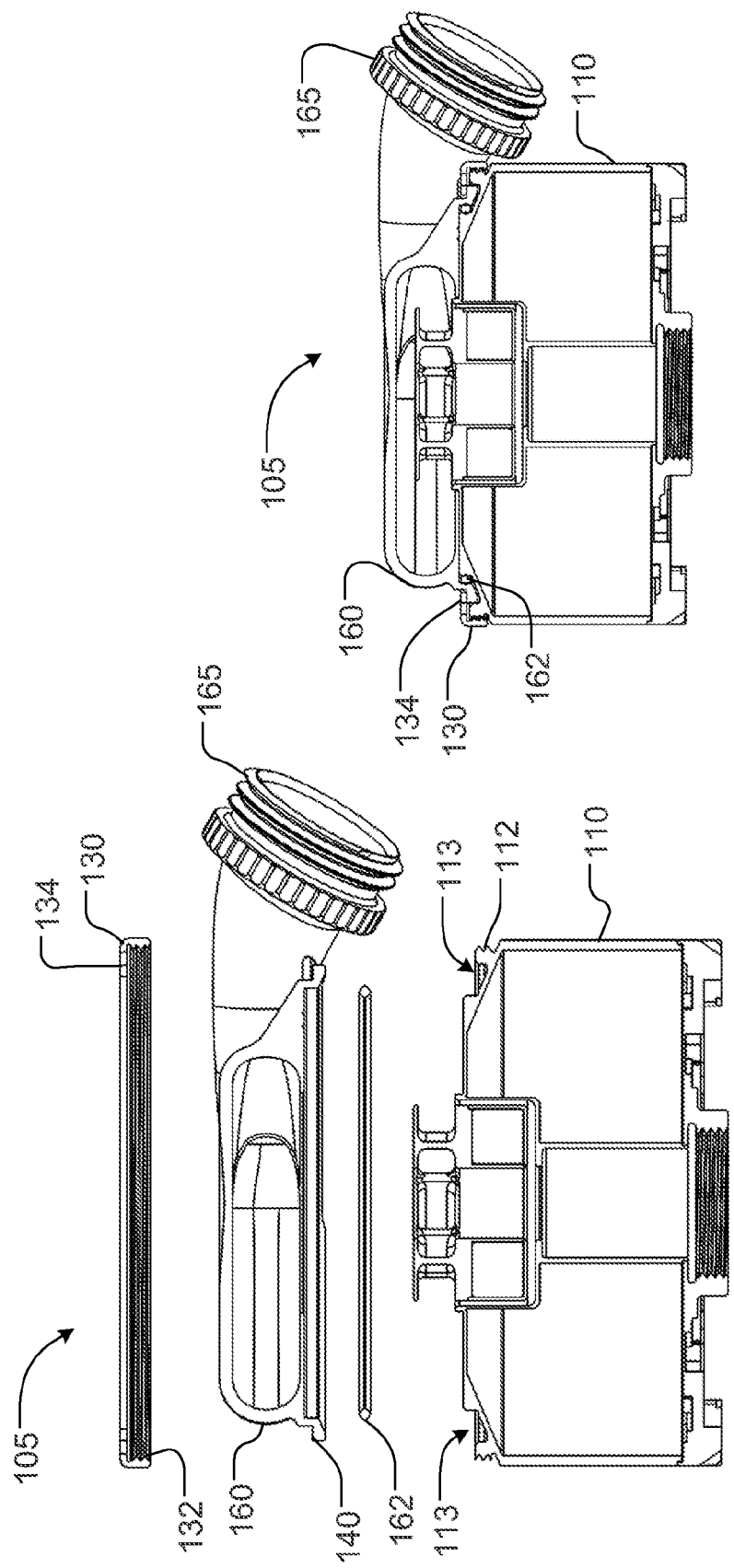

MODULAR IMPLANTABLE MEDICAL PUMP

CROSS-REFERENCE TO RELATED APPLICATIONS

This application claims priority to and the full benefit of U.S. Provisional Patent Application No. 61/606,767, filed Mar. 5, 2012 and titled "Modular Implantable Medical Pump," which is incorporated herein by reference in its entirety for all purposes.

TECHNICAL FIELD

This document relates to modular implantable medical pumps, such as ventricular assist blood pumps. This document also describes a method of calibrating implantable medical pumps.

BACKGROUND

The human heart is a complex and critical pump. Various pathologies can make the heart become dysfunctional, acutely or chronically. Heart failure can be treated with pharmacologic therapy and/or heart transplantation. Mechanical assistance is another therapeutic option for heart failure. For example, an afflicted person waiting to receive a transplant may receive mechanical assistance until a donor heart is available.

Blood pumps are commonly used to provide mechanical assistance or augmentation to the pumping performed by the left and/or right ventricles of the heart. For example, an implantable pump can be connected in parallel with the person's heart and implanted adjacent to the heart, in contact with the heart, or in a remote location such as the abdomen and inside or outside of the thoracic cavity in the chest area. A blood pump supplementing a ventricle is known as a ventricular assist device, or VAD. A VAD is useful when the ventricle alone cannot provide adequate blood flow. A pump can also completely replace the function of a ventricle.

SUMMARY

In a general aspect, a blood pump includes a coupling interface to couple to any of a plurality of different inflow cannulas.

In another general aspect, a blood pump includes a coupling interface to couple to any of a plurality of different pump covers that define an outflow port. The different pump covers can each define a volute for the blood pump.

In another general aspect, a blood pump comprises a motor housing and a pump cover that defines an outlet. The pump cover is rotatable relative to the motor housing to change a position of the outlet relative to the pump cover.

In another general aspect, a blood pump defines a blood flow path and includes textured surfaces that promote growth of a biologic layer on surfaces in the blood flow path. In some implementations, the textured surfaces are included only on components that are removable from a pump housing that includes the motor of the pump.

In another general aspect, a method of calibrating a blood pump includes coupling to the blood pump a calibration component that has substantially equivalent characteristics to a pump component that has a textured surface. In some implementations, the calibration component has a smooth surface in the region where the pump component has the textured surface. In some implementations, the calibration component has a textured surface in the region where the pump component has the textured surface.

In another general aspect, an implantable medical pump system includes a blood pump including a pump housing defining a passage therethrough and a rotor within the passage. The blood pump further includes one or more elements at least partially contained within the pump housing adapted to actuate the rotor to drive fluid though the passage. The pump housing includes at least one coupling feature. The system further includes an inflow cannula defining a lumen therethrough. The inflow cannula is adapted to be mechanically coupled to the at least one coupling feature.

Implementations may include one or more of the following features. For example, at least a portion of the inflow cannula extends into the passage when the inflow cannula is attached to the at least one coupling feature. The inflow cannula includes a textured blood-contacting surface. The textured blood-contacting surface includes sintered titanium powder. The textured surface is disposed on at least a portion of an outer diameter of the inflow cannula and at least a portion of an inner diameter of the inflow cannula. Substantially all of the blood-contacting surfaces of the inflow cannula include a textured coating. The inflow cannula is adapted to extend out from the pump housing when coupled to the at least one coupling feature such that a portion of the inflow cannula is adapted to traverse the myocardium of the heart. The inflow cannula includes: a first portion having a length sufficient to traverse a heart wall, the lumen extending through the first portion; an exterior thread pattern to mate with an interior thread pattern of the blood pump, the first portion protruding from the blood pump when the exterior thread pattern engages the interior thread pattern of the blood pump; and a second portion having a generally cylindrical outer surface received inside the passage of the blood pump when the exterior thread pattern engages the interior thread pattern of the blood pump, the second portion having a smaller outer diameter than the first portion. The inflow cannula is adapted to extend along at least 50% of the length of the passage when mechanically coupled to the at least one coupling feature. The passage defines a rotor well that receives the rotor, and the inflow cannula is adapted to extend to the rotor well when mechanically coupled to the at least one coupling feature. The system includes multiple inflow cannulas each adapted to be reversibly mechanically coupled to the at least one coupling feature such that at least a portion of the flow cannula extends into the passage, at least two of the inflow cannulas having different lengths. At least a first inflow cannula is adapted for traversing the myocardium of a left ventricle and a second inflow cannula is adapted for traversing the myocardium of a right ventricle. The system further includes a mounting cuff adapted to mechanically couple the pump housing to the myocardium of a heart, the mounting cuff comprising an inner surface adapted to fit around an outer perimeter of the inflow cannula or the pump housing. The system further includes a pump cover adapted to be mechanically coupled to the pump housing, the pump cover comprising a textured blood-contacting surface. The system further includes a pump cover adapted to be mechanically coupled to the pump housing, and the pump cover is free of textured blood-contacting surfaces. The at least one coupling feature includes a thread and the inflow cannula includes a corresponding thread. The system further includes one or more tools to connect the inflow cannula to the pump housing with a predetermined amount of torque. The at least one coupling feature and the inflow cannula comprise corresponding snap and mating surfaces. The lumen is tapered.

In another general aspect, a method of calibrating an implantable medical pump includes attaching a blood pump to a calibration cannula that approximates an inflow cannula for the blood pump. The method may include attaching the blood pump to a calibration cover that approximates a pump cover for the blood pump. The calibration cannula and calibration cover have smooth surfaces corresponding to the regions where the inflow cannula and pump cover have textured surfaces. The blood pump includes a pump housing defining a passage therethrough and a rotor within the passage. The pump housing at least partially contains one or more elements adapted to actuate the rotor to drive fluid through the passage. The method includes operating the blood pump in a calibration fluid while the motor is attached to the calibration cannula, and recording calibration variables based on a flow, a pressure, a speed, an operational power, or a combination thereof of the calibration fluid pumped by the blood pump. The method includes detaching the blood pump from the calibration cannula after operating the blood pump in the calibration fluid.

Implementations may include one or more of the following features. For example, the method further includes storing the recorded calibration variables in a memory associated with the implantable medical pump. The method further includes cleaning the blood pump after operating the blood pump in the calibration fluid. The method further includes attaching the inflow cannula to the blood pump motor after detaching the calibration cannula. Attaching the blood pump to the calibration cannula that approximates the inflow cannula for the blood pump includes attaching to the blood pump a calibration cannula that has a smooth or textured inner surface that defines a lumen, the inflow cannula having a textured surface that defines a lumen, the textured surface that defines the lumen of the inflow cannula comprising a powdered metal coating. The lumen of the calibration cannula and the lumen of the inflow cannula have dimensions that are substantially equal or are produced by the same manufacturing process. The method further includes attaching a calibration cover to the pump housing prior to operating the blood pump in the calibration fluid, the calibration cover approximating a pump cover for the blood pump and having a smooth or textured surface corresponding to a region where the pump cover has a textured surface. The calibration cover and the pump cover each define a volute, the calibration cover has a smooth or textured surface that defines the volute of the calibration cover, and the pump cover has a textured surface that defines the volute of the pump cover, the textured surface that defines the volute of the pump cover comprising a powdered metal coating. The volute of the calibration cover and the volute of the pump cover have dimensions that are substantially equal. The method further includes detaching the calibration cover from the pump housing after operating the blood pump in the calibration fluid. The method further includes attaching the pump cover to the pump housing after detaching the calibration cover. The blood pump defines a blood flow path, and the pump housing does not include any surfaces having a powdered metal coating in the blood flow path. The blood pump is packaged with one or more inflow cannulas. The one or more inflow cannulas each comprise: a first portion having a length sufficient to traverse a heart wall; an exterior thread pattern to mate with an interior thread pattern of the blood pump, the first portion protruding from the blood pump when the exterior thread pattern engages the interior thread pattern of the blood pump; and a second portion having a generally cylindrical outer surface received inside the passage of the blood pump when the exterior thread pattern engages the interior thread pattern of the blood pump, the second portion having a smaller outer diameter than the first portion. The blood pump may be packaged with one or more tools for attaching the one or more inflow cannulas to the motor. The blood pump may be assembled with a particular inflow cannula at the manufacturing facility. The pump housing includes smooth surfaces. The pump housing does not include any textured surfaces that promote tissue deposition. The textured surface of the inflow cannula or the pump cover includes a surface formed of a sintered titanium powder.

In another general aspect, a blood-pump inflow cannula includes a first portion having a length sufficient to traverse a heart wall. The inflow cannula also includes an exterior thread pattern along an exterior surface of the blood-pump inflow cannula to mate with an interior thread pattern of a passage of a blood pump, the first portion protruding from the blood pump when the exterior thread pattern engages the interior thread pattern of the blood pump. The inflow cannula includes a second portion opposite the first portion having a generally cylindrical outer surface received inside the passage of the blood pump when the exterior thread pattern engages the interior thread pattern of the blood pump, the second portion having a smaller outer diameter than the first portion. The blood-pump inflow cannula defines a lumen extending through the first portion and the second portion.

Implementations may include one or more of the following features. For example, the first portion has a tapered inner diameter. An outer surface of the second portion includes grooves. The outer surface of the second portion includes a ridge. The ridge includes grooves. The inflow cannula may be packaged separately from a blood pump or assembled at the manufacturing facility.

In another general aspect, a blood-pump-inflow-cannula attachment socket includes a body defining a cavity having a cylindrical inside surface, the cylindrical inside surface generally corresponding to an outer surface of a blood-pump inflow cannula, the body further comprising a plurality of grooves or projections that interlock with corresponding ridges, grooves, or notches of a blood-pump inflow cannula.

In some implementations, the body includes projections extending from a rim of the cavity and corresponding to notches in a ridge of a blood-pump inflow cannula.

In another general aspect, a wrench system includes the blood-pump-inflow-cannula attachment socket described above. In some implementations, the wrench in the wrench system is a torque-limiting wrench or a torque-measuring wrench.

In another general aspect, an implantable medical pump system includes a blood pump comprising a pump housing defining a passage therethrough and a rotor within the passage. The pump housing at least partially contains one or more elements adapted to actuate the rotor to drive fluid through the passage, and the pump housing includes at least one threaded element. The implantable medical pump system includes an inflow cannula defining a lumen therethrough, and the inflow cannula has a threaded exterior adapted to mate with the at least one threaded element.

Implementations may include one or more of the following features. For example, the at least one threaded element defines a lower surface of the pump housing. At least one threaded element is adapted to rotate with respect to a remainder of the pump housing given a sufficient torque application. At least one threaded element is held against the remainder of the pump housing by a capture ring. At least one threaded element includes one or more grooves, notches, or ridges. One or more grooves, notches, or ridges have a surface oriented generally in a plane including an axis of the threads. At least a portion of the inflow cannula extends into the passage when the inflow cannula is attached to the at least one coupling feature. The inflow cannula includes a textured blood-contacting surface. The textured blood-contacting surface includes sintered titanium powder.

In another general aspect, an implantable medical pump system includes a pump housing defining a passage therethrough and a rotor at least partially disposed in the passage. The pump housing at least partially contains one or more elements configured to actuate the rotor to drive fluid through the passage. The implantable medical pump system includes an inflow cannula that is removably attachable to the pump housing. The inflow cannula has an inner surface that defines a lumen through the inflow cannula, and the inner surface of the lumen has a textured blood-contacting surface. The implantable medical pump system includes a pump cover that is removably attachable to the pump housing. The pump cover has an inner surface that defines a volute, and the inner surface of the pump cover has a textured blood-contacting surface.

In various embodiments, one or more of the blood-contacting surfaces is textured.

The textured surfaces may be made from a metal, such as a powdered metal, or a polymer. In various embodiments, the textured surface is a sintered titanium beaded surface. In various embodiments, the roughness of the textured surface is measured by determining a Ra value, and the Ra value of the textured surface is greater than 100 millionths of an inch, greater than 200 millionths of an inch, or greater than 500 millionths of an inch. In some embodiments, the textured surface has a Ra value of at least 200 millionths of an inch, at least 500 millionths of an inch, or at least 1000 millionths of an inch. In some embodiments, the textured surface has a Ra value of less than 10,000 millionths of an inch, less than 5,000 millionths of an inch, less than 1,000 millionths of an inch, or less than 500 millionths of an inch. In some embodiments, the smooth surfaces can have a Ra value of less than 100 millionths of an inch. The pump cover may also include textured blood-contacting surfaces. The one or more of the blood-contacting surfaces may be modified or treated in other manner. For example, the blood-contacting surfaces may comprise a porous coating or relatively hard coating.

Implementations may include one or more of the following features. For example, the lumen extends into the passage when the inflow cannula is attached to the pump housing. The textured blood-contacting surfaces comprise a powdered metal coating, and the pump housing does not have any blood-contacting surfaces that comprise a powdered metal coating. The powdered metal coating may include a sintered titanium coating. The inflow cannula, the pump housing, and the pump cover define a blood flow path through the pump, and the pump housing defines a rotor well that receives a portion of the rotor; and textured blood-contacting surfaces are disposed along the entire blood flow path except the rotor well. A textured surface is disposed on at least a portion of an outer surface of the inflow cannula and at least a portion of an inner surface of the inflow cannula. The textured surface is disposed on at least a portion of an outer diameter of the inflow cannula and at least a portion of an inner diameter of the inflow cannula. Substantially all of the blood-contacting surfaces of the inflow cannula include a textured coating. The inflow cannula is dimensioned to extend along at least 50% of the length of the passage when the inflow cannula is received in the passage. The passage defines a rotor well that receives the rotor, and the inflow cannula is adapted to extend to the rotor well when mechanically coupled to the at least one coupling feature.

The details of one or more embodiments are set forth in the accompanying drawings and the description below. Other features, objects, and advantages will be apparent from the description and drawings, and from the claims.

DESCRIPTION OF DRAWINGS

FIGS. 2D-2J are various cutaway and/or perspective views of pump covers according to a particular embodiment.

FIG. 3A is a cross-sectional view of an implantable medical pump having an inflow cannula according to a second embodiment. FIG. 3B is an expanded perspective view of the implantable medical pump system showing how the inflow cannula of FIG. 3A is attached to the pump housing.

FIG. 4A is a cross-sectional view of depicting a single threaded attachment between the pump housing and the inflow cannula. FIG. 4B is an expanded perspective view showing how the inflow cannula is attached to the pump housing.

FIG. 5A is a cross-sectional view of depicting a multi-component threaded attachment between the pump housing and the inflow cannula. FIG. 5B is an expanded perspective view showing the arrangement of the components of this attachment feature.

FIG. 6A is a cross-sectional view of depicting a multi-component threaded attachment between the pump housing and the inflow cannula. FIG. 6B is an expanded perspective view showing the arrangement of the components of this attachment feature.

FIGS. 10H to 10M illustrate an adjustable pump cover of the implantable medical pump of FIG. 1A.

DETAILED DESCRIPTION

Figure 1A:
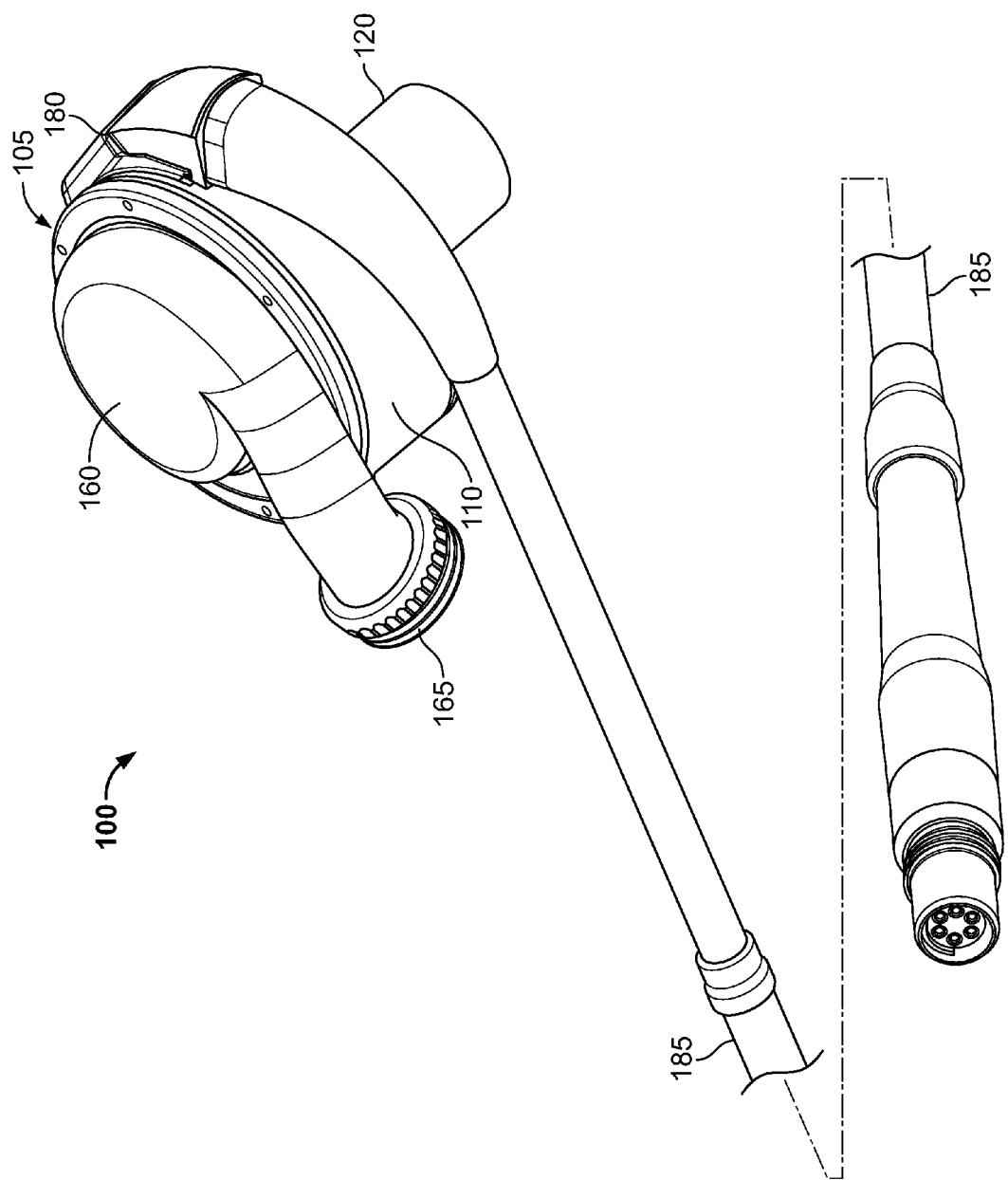
FIG. 1A is a perspective view of an exemplary implantable medical pump.
Figure 1B:
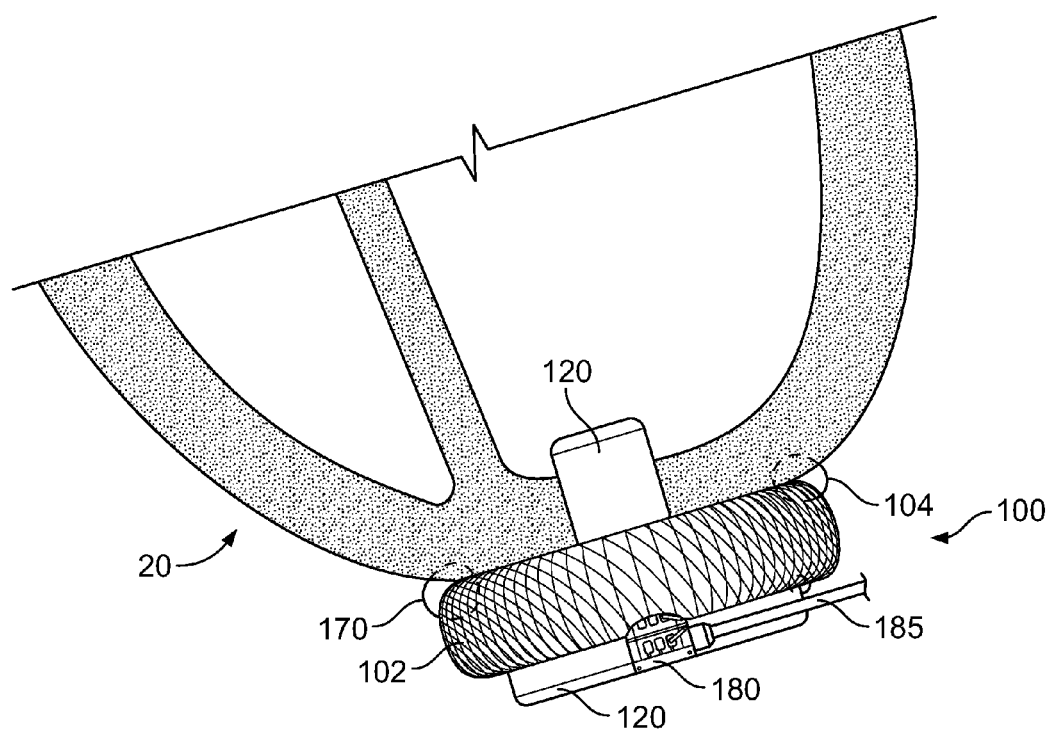
FIG. 1B illustrates an example of how an implantable medical pump can be secured to a heart.

FIG. 1A illustrates an example of an implantable medical pump system 100 having a modular design that includes an inflow cannula 120 that can be separated and reattached to a pump housing 110 of a blood pump 105. Moreover, a plurality of inflow cannulas 120 having different features can each be adapted for modular attachment to the pump housing 110 to adapt the implantable medical pump system 100 for a particular use. For example, some inflow cannulas can be adapted to assist the left ventricle, as illustrated in FIG. 1B, while other inflow cannulas can be adapted to assist the right ventricle.

Different patients can have heart-wall thicknesses that differ. These differences may not be apparent until the time of implantation. Moreover, a cannulation location for a particular patient may not become apparent until the time of implantation. Different chambers of the heart can have varying flow pattern, which can also impact the type of inflow cannula used for a given implantation site. Different inflow cannulas can thus have different materials or coating, can have different diameters, can have different lengths, and/or can extend from the motor's base at different angles, such that each inflow cannula is adapted for a particular use and/or patient. Modular attachment of the inflow cannula 120 to the blood pump 105, whether by having a threaded connection, a snap-fit connection, a welded connection, etc., can permit a clinician to adapt a blood pump for a particular use.

The inflow cannula 120 can include a blood-and-tissue-compatible textured surface 870 (shown in FIGS. 8A through 8F) and can extend into a passage (e.g., 214 shown in FIG. 2A) defined in the pump housing 110. The blood-and-tissue-compatible textured surface 870 can encourage or promote the formation and adherence of a biologic lining. In some embodiments, the inflow cannula 120 is adapted to extend into at least fifty percent of the passage 214 of the pump housing 110 when mechanically secured to the pump housing 110. For example, the inflow cannula 120 can extend inward past the electronics of the blood pump (e.g., stator, control electronics, PCB). In certain embodiments, the inflow cannula is adapted to extend to a rotor well 252 (shown in FIG. 2A) that contains a rotor 255 (shown in FIG. 2A).

The blood pump 105 can be calibrated prior to use in order to ensure that the blood pump is accurately controlled and provides appropriate flow estimations to the clinician when implanted. Each blood pump 105 that is manufactured can be individually calibrated. In some implementations, the blood pump 105 is calibrated using a calibration cannula and/or a calibration cover different from the inflow cannula 120 and/or the pump cover 160 that are actually implanted with the blood pump 105. Using a different cannula or cover for calibration avoids the need to clean (e.g., sterilize) the inflow cannula 120 and/or the pump cover 160 as a result of calibration. In some instances, cleaning (e.g., sterilizing) a textured surface, such as the textured surface 670 of FIGS. 6A and 6B, after use in calibration may be difficult or time consuming. For example, during the calibration process, textured surfaces may collect contaminants that are difficult to dislodge. Because the pump housing 110 permits modular attachment of different inflow cannulas and pump covers, the blood pump 105 may be calibrated with a calibration cannula and/or calibration cover having smooth surfaces, which are easier to clean than textured surfaces. The blood pump 105 is then implanted with the inflow cannula 120 and/or the pump cover 160 having textured surfaces.

A pre-implantation calibration method can include attaching the pump housing 110 to a calibration cannula (not shown) and/or a calibration cover (not shown), operating the blood pump in the calibration fluid, separating the calibration cannula and/or the calibration cover from the pump housing 110, and cleaning (e.g., sterilizing) the pump housing 110. The calibration cannula can have the same structure (e.g., the same dimensions) as the inflow cannula 220 shown in FIGS. 2A-2C, but in one or more regions, the calibration cannula can have a surface texture that is different from the surface texture of the inflow cannula 220. For example, the interior and/or exterior of the calibration cannula can be smooth surfaces, and the interior and/or exterior of the inflow cannula 220 can be textured surfaces. The calibration cover can have the same structure (e.g., the same dimensions) as the pump cover 260 shown in FIGS. 2D-2J, but in one or more regions, the calibration cover can have a surface texture that is different from the surface texture of the pump cover 260. For example, the interior of the calibration cover that defines a volute can have smooth surfaces, and the interior of the pump cover 260 that defines a volute can have textured surfaces.

The calibration cannula and/or calibration cover can affect liquid flow rates in substantially the same manner as the inflow cannula 120 and/or the pump cover 160. Operation of the blood pump 105 with the calibration components can be within a predetermined acceptable tolerance of operation of the blood pump 105 with clinical components. For example, performance of the blood pump 105 with the calibration components having smooth surfaces may be within 20% or less, 10% or less, or 5% or less of the performance of the blood pump 105 with clinical components having textured surfaces.

The use of the calibration cannula and/or calibration cover can avoid exposing surfaces having a geometry that might capture contamination to sources of contamination from the calibration procedure. After the calibration, the pump housing 110 can be attached to the pump cover 160 and/or the inflow cannula 120. The pump cover 160 and/or inflow cannula 120 can be of clinical grade, but may also be nearly identical to the calibration cannula and/or calibration cover.

As noted above, a textured surface, can present a contamination risk due to the added difficulty of cleaning a textured surface as compared to cleaning a smooth surface. The modular design of the blood pump 105, however, can reduce the contamination risk caused by pre-implantation calibration methods. For example, the inflow cannula 120 of the modular blood-pump system provides a textured surface extending into the pump housing 110, thus minimizing smooth surfaces exposed to blood when the blood pump 105 is implanted. Use of a calibration cannula having a smooth interior surface instead of a textured surface during calibration reduces a contamination risk associated with pre-implantation calibration procedures. An example of a pre-implantation calibration method is discussed in further detail below in reference to FIG. 9.

The implantable medical pump system can be provided as a kit including a blood pump 105 (including a pump housing 110) and one or more inflow cannulas. The kit can further include one or more pump covers 160 as separate components. In some embodiments, the kit can include one or more tools configured to help a clinician connect the inflow cannula and/or pump cover to the pump housing 110. For example, a connection socket 1000 and torque wrench 1010 are described below in reference to FIGS. 10A-10G.

A system and/or kit including a plurality of inflow cannulas and/or pump covers (and optionally one or more tools to attach the inflow cannulas and/or pump covers) permits a clinician to make a determination of the particular implantation site and the type of cannula or cannula position during the implantation procedure once the clinician is observing the patient's anatomy. One or more tools can ensure that the selected inflow cannula and/or pump cover is connected appropriately (e.g., with a desired amount of torque). The tool(s) and/or inflow cannulas and/or pump covers adapted for attachment to a pump housing 110 can also be sold separately and/or held in stock by a hospital or clinician.

In some implementations, the system or kit can include a component that can be rotated to change the position of an outflow port 165 relative to the pump housing 110 given a predetermined amount of torque application. For example, the pump cover 160 may define the outflow port 165 for the blood pump 105. The pump cover 160 can be rotated relative to the pump housing 110 to alter the position of the outflow port 165 with respect to the pump housing 110. In some implementations, the pump cover 160 can be replaced with a different cover having an outflow port with a different trajectory.

Rotation of the pump cover 160 or replacement of the pump cover 160 can permit a clinician to position the outflow port for various implantation positions, implantation techniques, and clinical applications. For example, the clinician may rotate the outflow conduit between a first position for use of the implantable medical pump 100 as a left ventricular assist device (LVAD), a second position for use as a right ventricular assist device (RVAD), and/or a third position for use in a biventricular assist device (BiVAD) configuration. Other positions may be used for, for example, ascending aorta anastomosis, descending aorta anastomosis, and other implantation configurations. Similarly, the position of outflow port 165 may be adjusted to accommodate implantation at the apex of the left ventricle (e.g., with an apical approach), or with the pump housing 110 spaced apart from the myocardial wall of the heart.

Implantable Medical Pump Assembly

The implantable medical pump assembly 100 can be a ventricular assist device (VAD). A VAD is a mechanical circulatory device that is used to partially or completely replace the function of a failing heart. Some VADs are intended for short term use, for patients recovering from heart attacks or heart surgery, while others are intended for long term use (e.g., months, years, or the remainder of a patient's life). VADS are often used for patients suffering from heart failure. VADs are designed to assist either the right (RVAD) or left (LVAD) ventricle, or both at once (BiVAD). Some assist devices are cannulated to the atria instead of the ventricles.

Referring to FIGS. 1A-1C and 2A-2C, the modular implantable medical pump assembly 100 can include a blood pump 105 having a pump housing 110 that defines a rotor well 252 (shown in FIGS. 2A-2C) that receives at least a portion of a rotor 255. The pump housing 110 also houses elements 290 (e.g., control electronics, stators, stator coils, electrical hardware) designed to actuate the rotor 255 to pump blood though a passage 214. The blood pump 105 can have a generally cylindrical shape. Inflow cannula 120 projects out of the blood pump 105 so that it may extend into a chamber of the heart, as shown in FIG. 1B. The selection of different inflow cannulas can permit the placement of the modular implantable medical pump assembly 100 at different locations. A heart contacting surface of the pump housing 110 can include a pump cap 230. The blood pump 105 also includes an outflow port 165 for expelling blood that has been drawn by the blood pump 105 from the interior chamber of the heart.

Figure 2A:
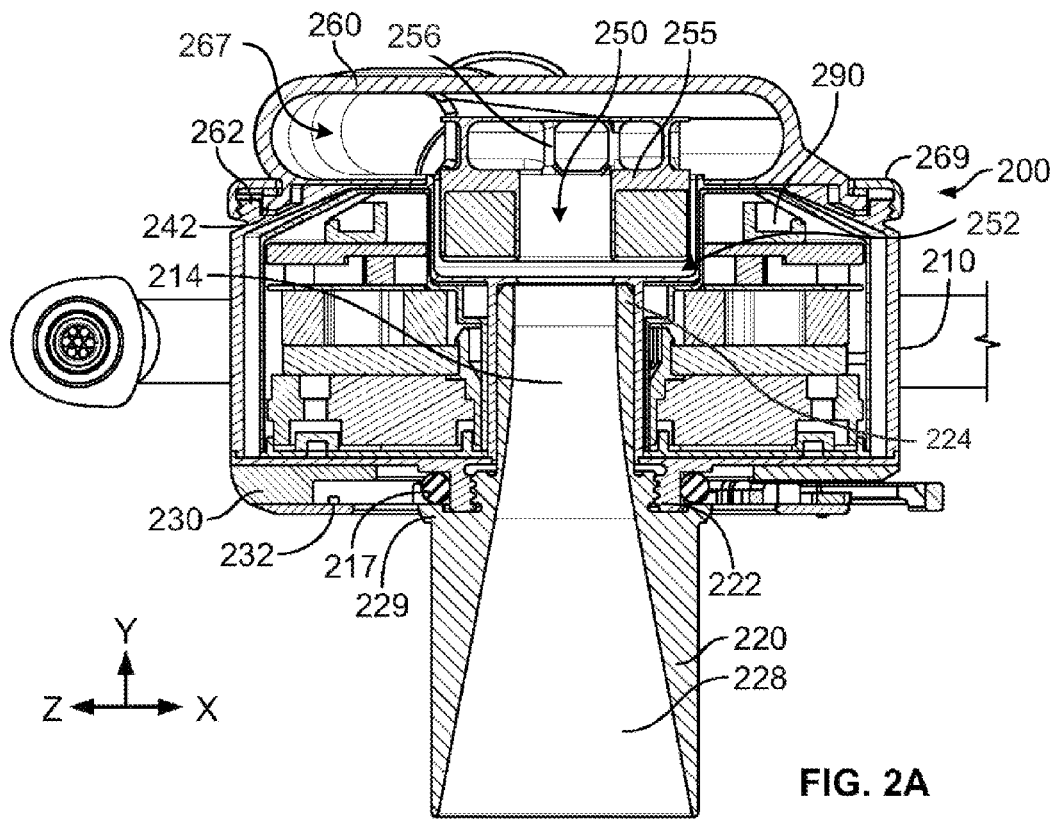
FIGS. 2A-2C are various cutaway views of the exemplary implantable medical pump shown in FIG. 1A.
Figure 2B:
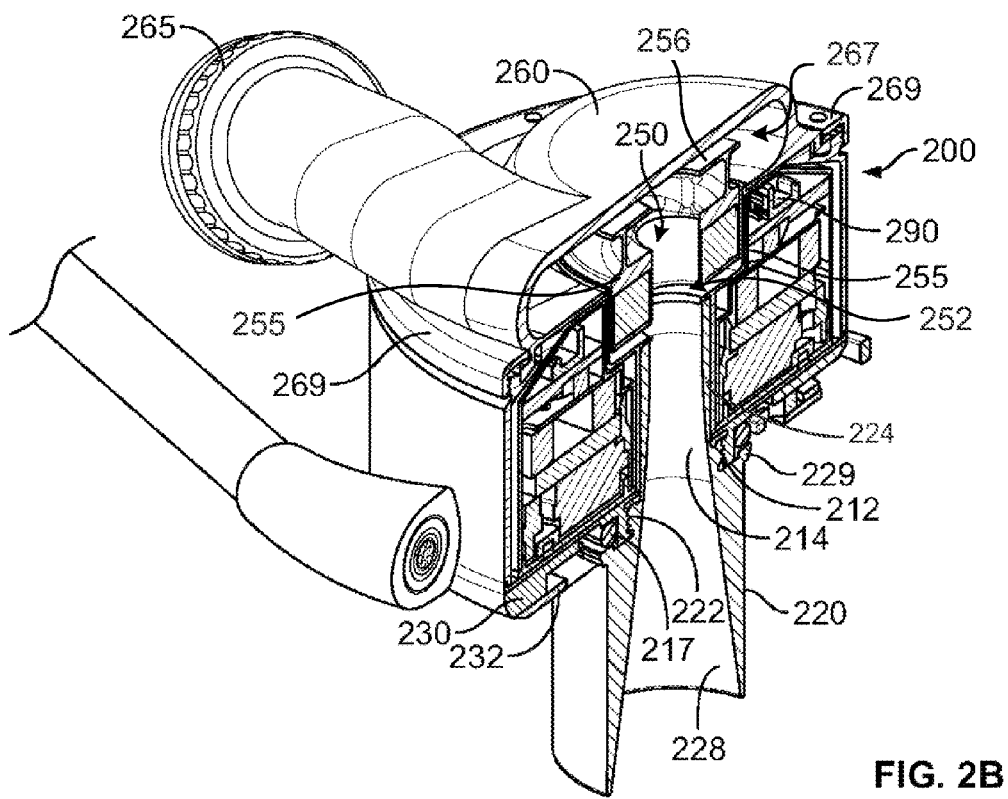
Figure 2C:
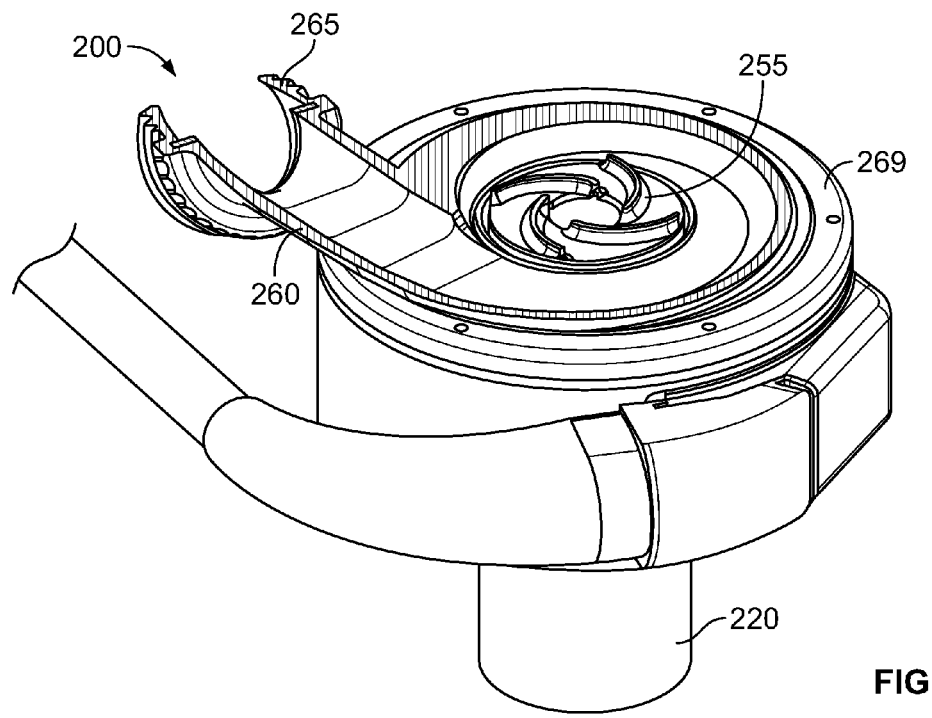
Figure 2D:
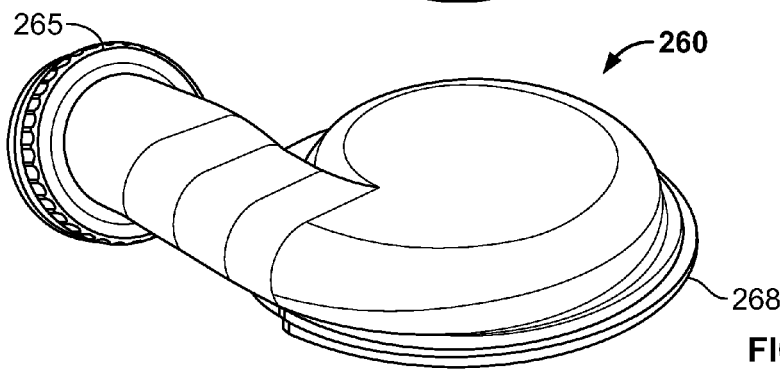
Figure 2E:
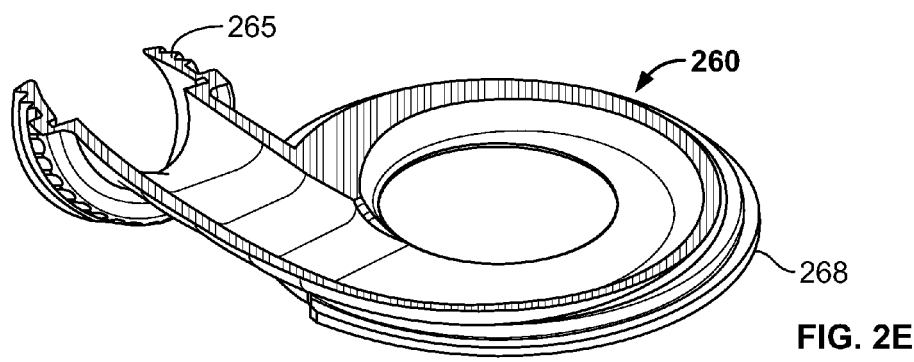
Figure 2J:
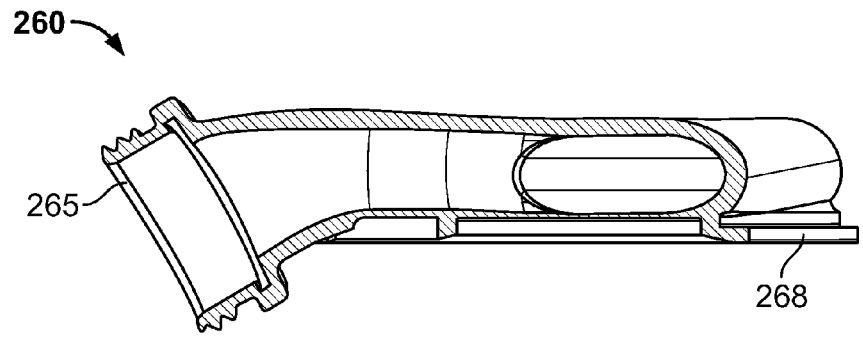

FIGS. 2A-2C illustrate an embodiment of an implantable medical pump 200 having a pump housing 210 defining a flow passage 214 therethrough and containing elements 290 (e.g., stator coils) adapted to drive the rotor 255 contained in a rotor well 252 of the flow passage 214. The pump housing 210 includes a pump cap 230 having a generally flat base. The pump cap 230 can have a generally cylindrical perimeter. The pump cap 230 can additionally include attachment features 232 that secure the pump housing 210 to an apical attachment cuff. The exemplary apical attachment cuff is an assembly that a clinician can attach to the myocardium to provide a method for attaching the implantable medical pump 200 to a heart. The apical attachment cuff can also providing a hemostatic seal. Apical attachment cuff are discussed in further detail in provisional patent application number 61/448,434, which is hereby incorporated by reference in its entirety. In some implementations, the apical attachment cuff fits over the inflow cannula 220 and engages exterior features of the inflow cannula 220 to couple to the implantable medical pump 200. A locking mechanism, such as a clip or other fastener can further secure the apical attachment cuff to the implantable medical pump 200.

The pump cap 230 can also include a coupling feature 212 for securing an inflow cannula 220 to the pump housing 210. In some embodiments, the apical attachment cuff 232 and the coupling feature 212 are machined into the pump cap 230 and/or the pump housing 210. In other embodiments, the coupling feature 212 is welded to the pump cap 230 and/or the pump housing 210.

The inflow cannula 220 is adapted to be connected to the coupling feature 212 of the pump housing 210 by a corresponding coupling feature 222. In the embodiments shown, the coupling feature 222 includes threads corresponding to threads in coupling feature 212. The inflow cannula is threaded into the pump housing 210 until the end of the inflow cannula 220 is seated in or against an opening of the rotor well 252. In the embodiment shown, the threaded attachment feature protrudes out from the pump housing 210 along a periphery of a flow passage 214 through the pump housing 210. This simple-thread coupling feature 212 featured in FIGS. 2A and 2B includes only a single leak pathway. The threaded connection may be designed such that a predetermined amount of torque can be used to secure the inflow cannula 220 to the pump housing 210 and thus mitigate the risk of auto rotation of the inflow cannula during use. In other embodiments, the coupling feature can be a snap-fit coupling feature. In addition to reversible coupling features, permanent coupling features are also contemplated (see FIG. 7 discussed below). For example, anchors can be positioned on the pump cap 230 and/or the inflow cannula 220 to stop back rotation. Moreover, one or more coupling features can be located within the flow passage 214. For example, the threaded connection can be along the flow passage 214.

At least a portion of the inflow cannula 220 extends into the flow passage 214. As shown, a first end 224 of the inflow cannula 220 extends into the flow passage 214 to rotor well 252. In some embodiments, the inflow cannula 220 extends along at least fifty percent of the length of the flow passage 214 when the inflow cannula is connected to the coupling feature 212.

The inflow cannula 220 defines a lumen 228 through which blood can travel when the implantable medical pump 100 is implanted and in operation. As discussed in detail below, particularly with regard to FIGS. 8A to 8F, the blood-contacting surfaces of the inflow cannula 220 can have a blood-and-tissue-compatible textured surface. A blood-and-tissue-compatible textured surface on the inside surface of the lumen 228 can thus extend into the flow passage 214 of the pump housing. As depicted in FIG. 2A, the lumen 228 can be tapered towards the pump housing 210. A tapered lumen can minimize flow disruptions (e.g., turbulence, swirl). In some embodiments, the lumen includes a gradual taper, which can be used to reduce the lumen opening to the appropriate diameter of the rotor and avoid a large pressure drops in the system that may affect pump efficiency. Moreover, a larger opening at the mouth of the lumen, which is placed within the cardiac chamber, can help prevent stenosis or occlusion as a result of the typical healing response to the injury created during implantation or due to inflow cannula malposition following implantation.

The inflow cannula can include a ridge 229 around its outer perimeter. A seal ring 217 can also be positioned between the ridge 229 and the pump cap 230. The ridge 229 can press the seal ring 217 between the inflow cannula 220 and the pump cap 230. A seal ring 217 can mitigate the risk of bodily fluids passing into the pump housing 210 through a thread/connection gap between the inflow and the housing.

The implantable medical pump 200 can also include a pump cover 260. FIGS. 2C-2J illustrate the pump cover 260 in greater detail, including various cutaway views of the pump cover 260. The pump cover 260 defines an outflow port 265, which can be located along the perimeter of the implantable medical pump 200. The pump cover 260 defines a volute 267, which is an interior volume in fluid communication with the outlet port 265. In some implementations, the volute 267 has a cross sectional volume that expands in a circumferential direction about the axis of rotation of the rotor 255. The volute 267 can convert kinetic energy of blood flow in the volute 267 to pressure at the outlet port 265. The rotor 255 has blades 256 that extend into the volute 267. The rotor 255 also defines a central opening 250 that admits blood through the rotor 255 into the volute 267.

Blood-contacting surfaces of the pump cover 260 can include blood-and-tissue-compatible textured surfaces, such as those discussed below with regard to the inflow cannula. As will be described further below, the blood-contacting pump components may include a textured surface, a smooth surface, or a combination thereof. The pump cover 260 can be secured to the pump housing 210 by a reversible coupling feature, such as corresponding threads 242 and 262. As shown in FIGS. 2A and 2B, the pump system can include an O-ring 269 that is secured to the pump housing 110 by threads 242 and 262 and holds a lip 268 of the pump cover 260 against the pump housing 210. The outflow port 265 can expel blood that has been drawn by the implantable medical pump 200 from the interior chamber of the heart and accelerated by the rotor 255 in the rotor well 252.

The coupling feature that secures the pump cover 260 to the pump housing 210 permits the pump cover 260 to be secured at any of multiple rotational orientations of the pump cover 260 with respect to the pump housing 210. In some implementations, the coupling feature can secure the pump cover 260 at any rotational position with respect to the pump housing 210, for example, at any incremental rotational position. The coupling feature may permit the pump cover 260 to be rotated relative to the pump housing while the pump cover is secured to the pump housing 210 with application of at least a predetermined amount of torque.

Because the pump cover 260 includes the outflow port 265, rotating the pump cover 260 relative to the pump housing 210 changes the position of the outflow port 265 relative to the pump housing 210. As shown, the pump cover 260 defines the entire volute 267. With the volute 267 entirely contained in the pump cover 260, the pump implantable medical pump 200 can produce the same flow characteristics with the pump cover 260 in any of various rotational orientations with respect to the pump housing 210.

The outflow port 265 can be fluidly connected via flexible conduit 167 (see FIG. 1C) to the aorta or another anatomical feature such that blood drawn from the heart can be expelled under pressure into the circulatory system of the user. In some implementations, the flexible conduit 167 can be rotated, bent, twisted, or otherwise oriented with respect to the blood pump 105 while the flexible conduit 167 is secured to the blood pump 105. As a result, the flexible conduit 167 accommodates implantation of the blood pump 105 at various positions relative to the heart 20.

Figure 3A:
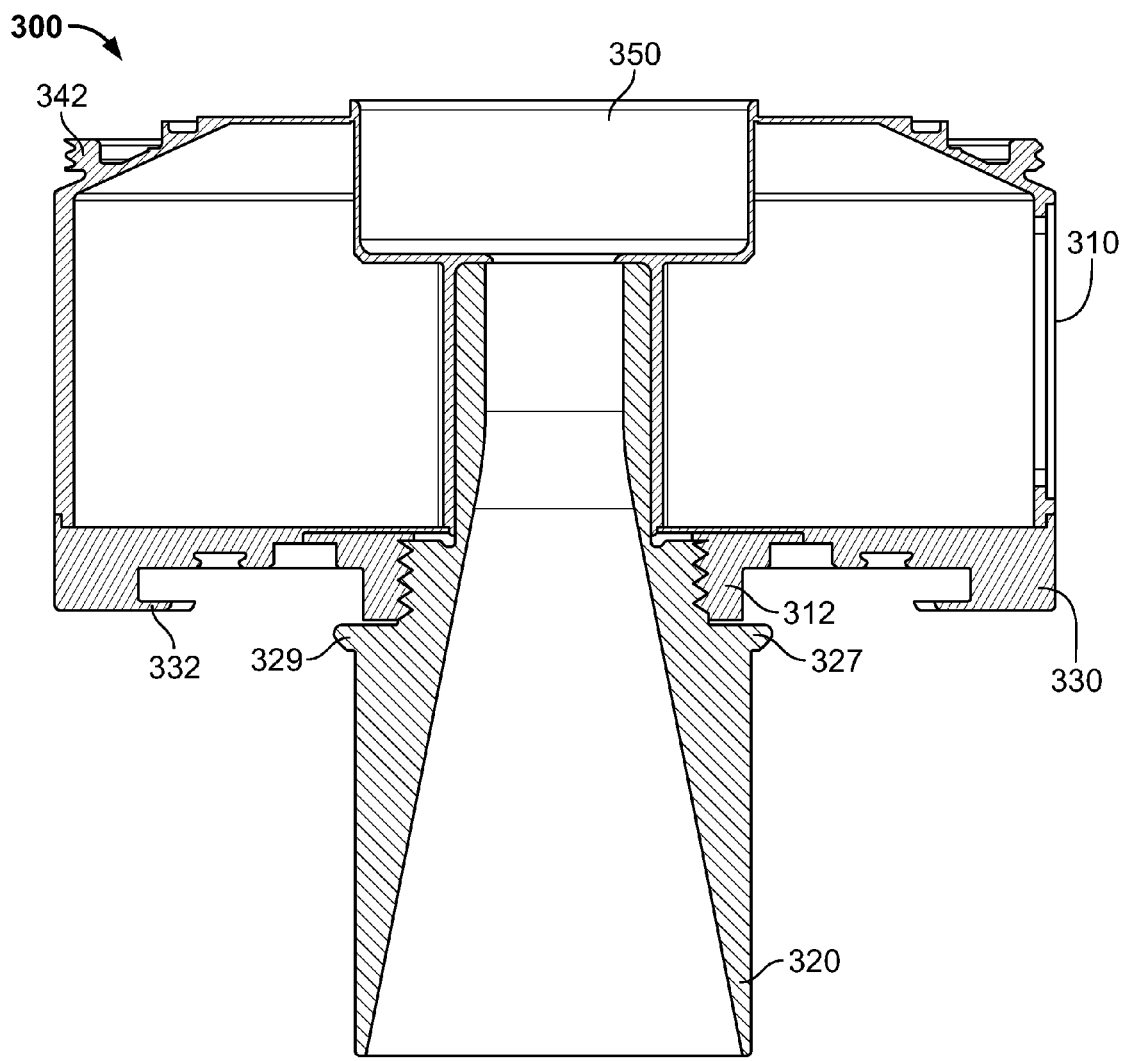
FIGS. 3A-3B illustrate an embodiment of an implantable medical pump having a single threaded attachment between the pump housing and the inflow cannula.
Figure 3B:
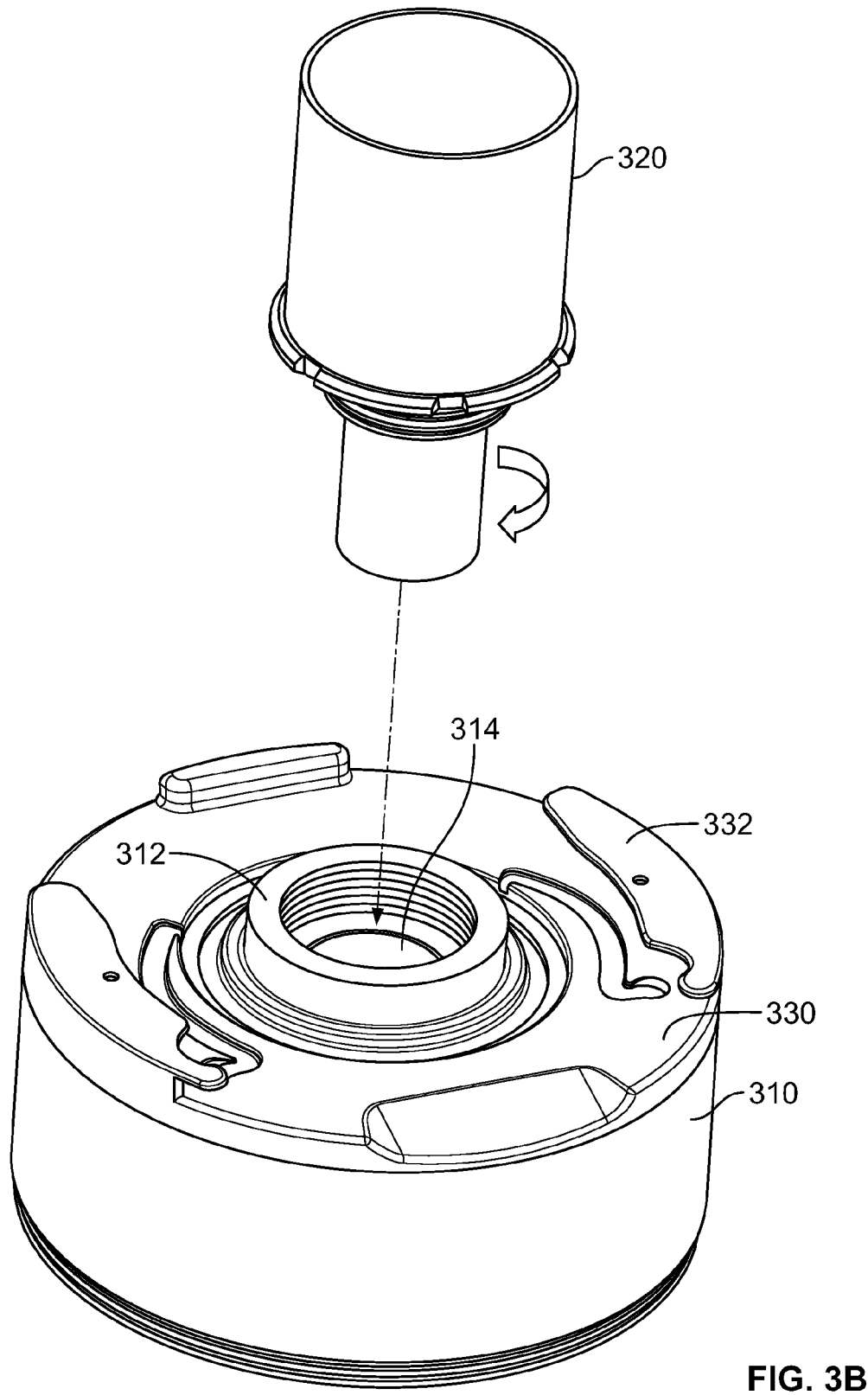

FIGS. 3A and 3B depict an implantable medical pump 300 according to a second embodiment having a similar construction to that of the embodiment of FIGS. 2A-2J. FIGS. 3A and 3B depict an inflow cannula 320 having a discontinuous ridge 329 around its outer perimeter. The grooves 327 in the discontinuous ridge 329 can permit a tool to easily grasp the inflow cannula for installing the inflow cannula to the pump housing 310. An example of such a tool is that shown in FIGS. 10A-10G, discussed below. The pump cap 330 can be machined with the threaded coupling feature 312 and/or the apical attachment cuff 332. The inflow cannula 320 can be threaded into the coupling feature 312 until one end of the inflow cannula 320 is positioned in the flow passage 314 and seated in or against an opening of the rotor well 350. The threaded connection between the inflow cannula 320 and the coupling feature 312 can be a single threaded connection. The threads of the inflow cannula 320 and the coupling feature 312 can be complementary so as to ensure a snug fit. A pump cover (not shown) can be secured to the pump housing via attachment feature 342.

Figure 4A:
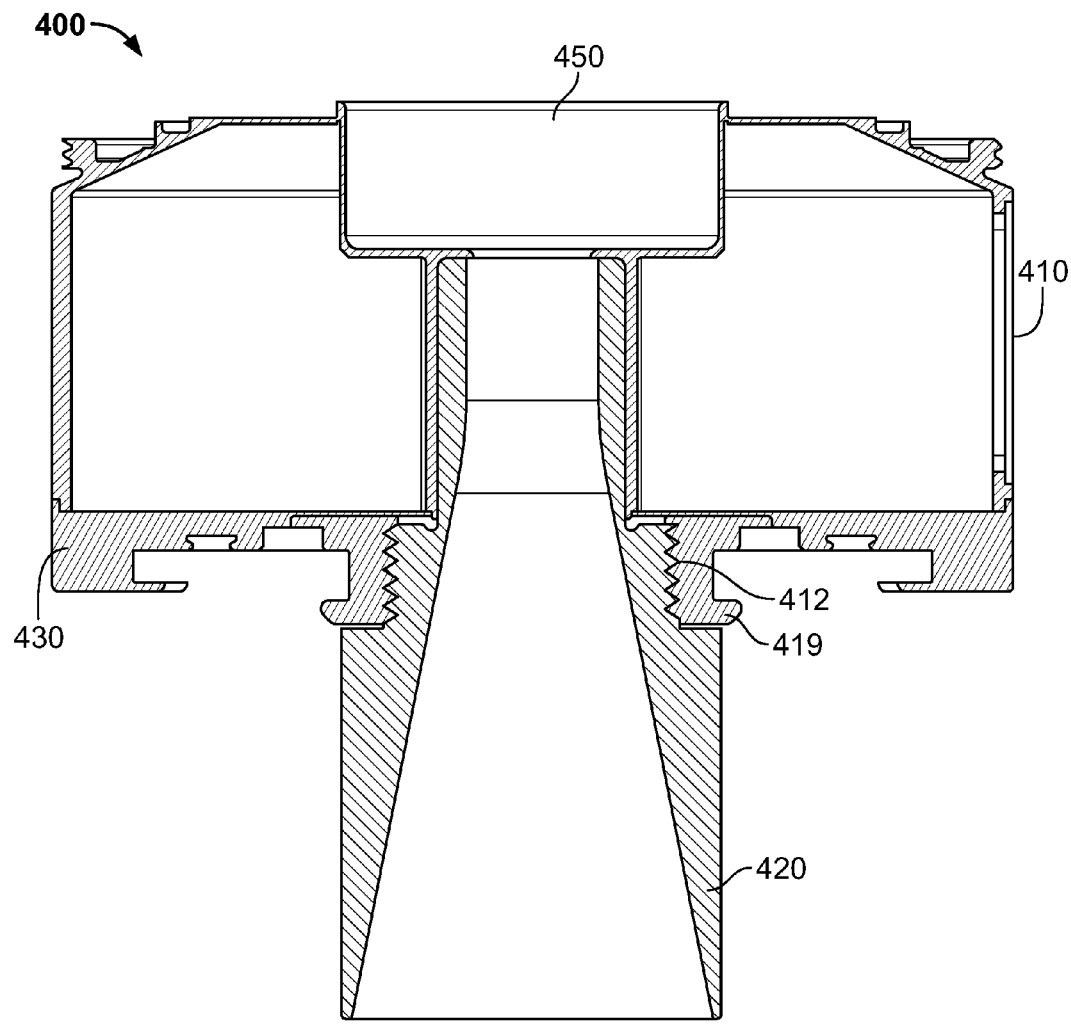
FIGS. 4A and 4B illustrate a second embodiment of an implantable medical pump system having a single threaded attachment between the pump housing and the inflow cannula.
Figure 4B:
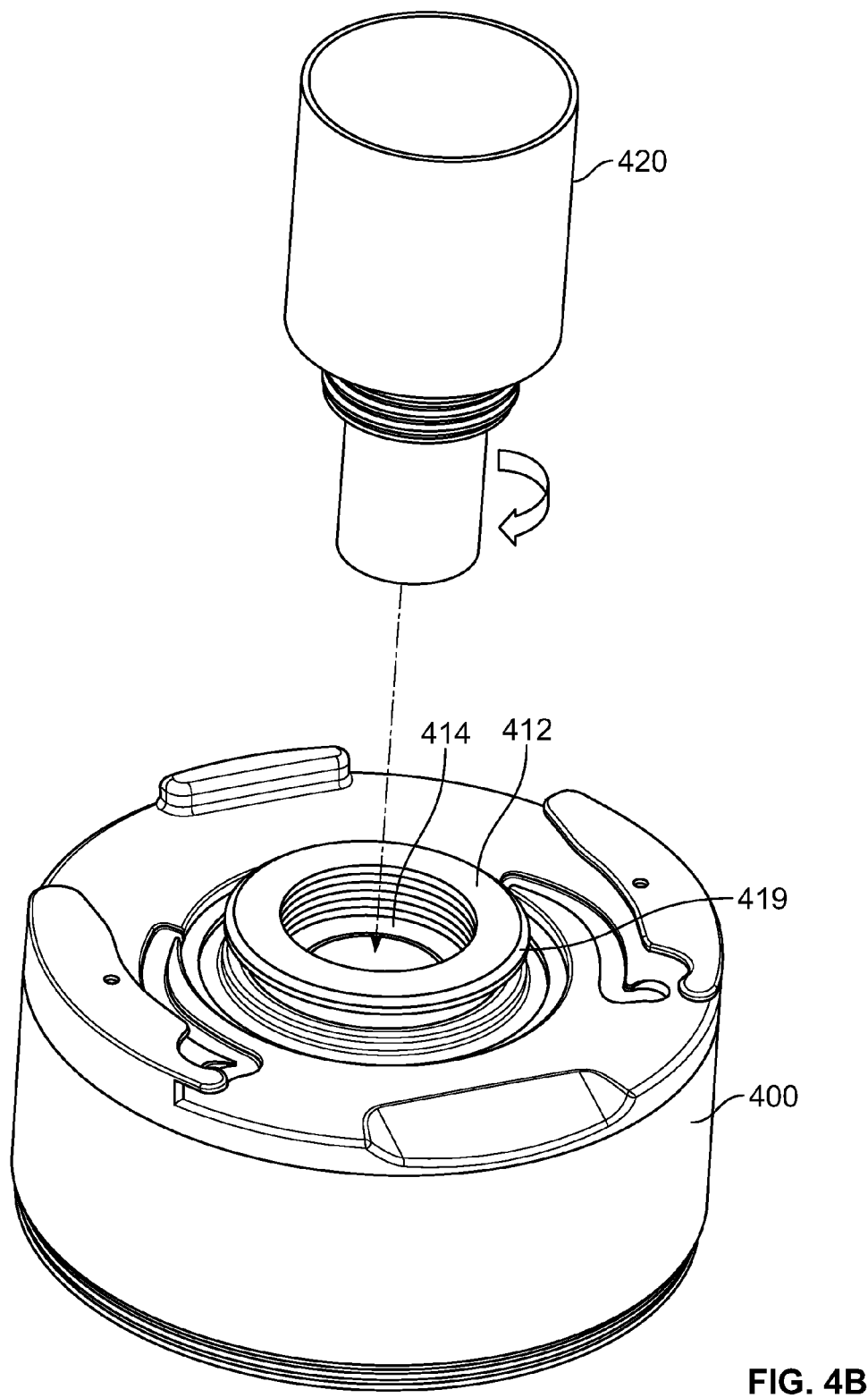

FIGS. 4A and 4B depict another embodiment of a blood pump system 400 having a similar construction to that of the embodiments of FIGS. 2A-2F and 3A-3B. FIGS. 4A and 4B also include a threaded attachment between the inflow cannula 420 and the threaded coupling feature 412 of the pump housing 410, but a ridge 419 is supplied as part of the coupling feature 412. The inflow cannula 420 can be threaded into the coupling feature 412 until one end of the inflow cannula 420 is positioned in the flow passage 414 and seated in or against an opening of the rotor well 450. The threaded connection between the inflow cannula 420 and the coupling feature 412 can be a single threaded connection. The threads of the inflow cannula 420 and the coupling feature 412 can be complementary so as to ensure a snug fit.

Figure 5A:
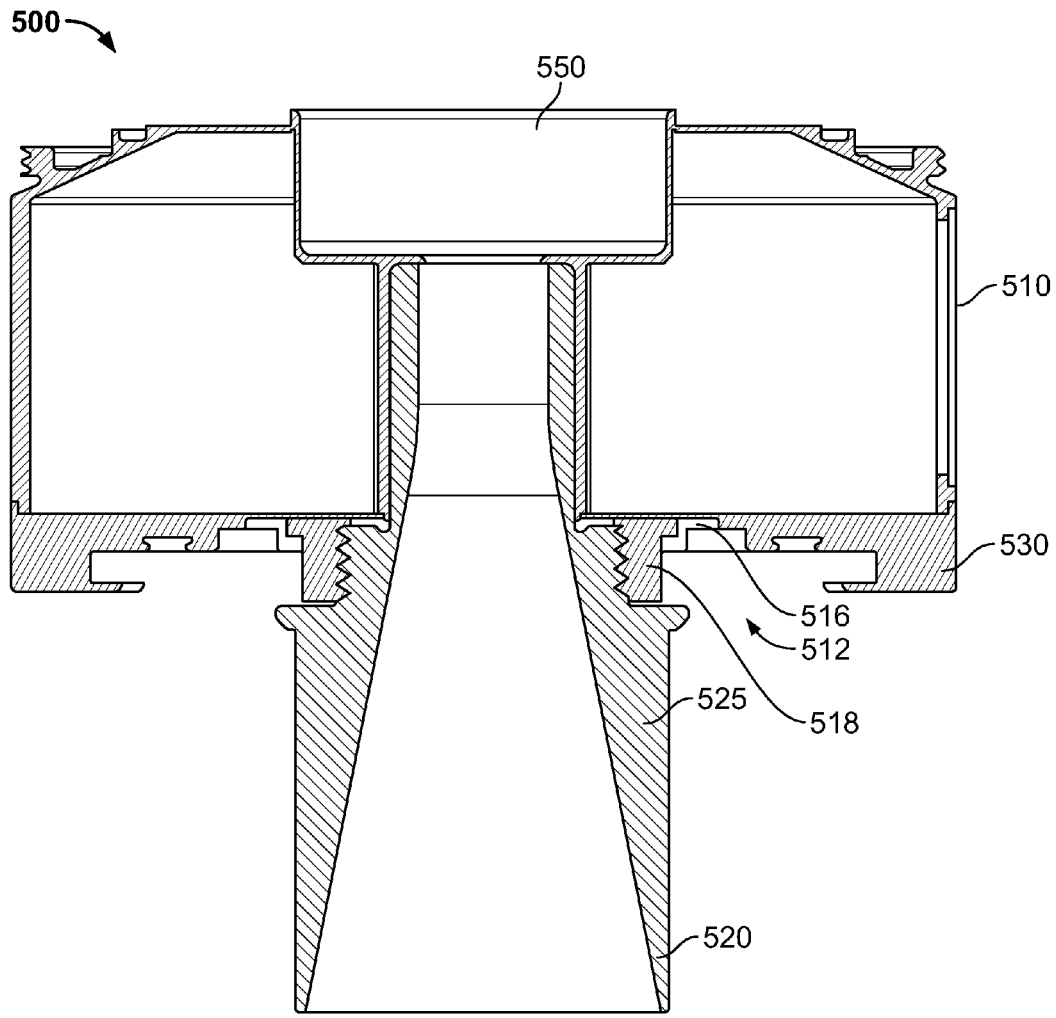
FIGS. 5A and 5B illustrate an embodiment of an implantable medical pump system having an inflow cannula having a multi-component threaded attachment.
Figure 5B:
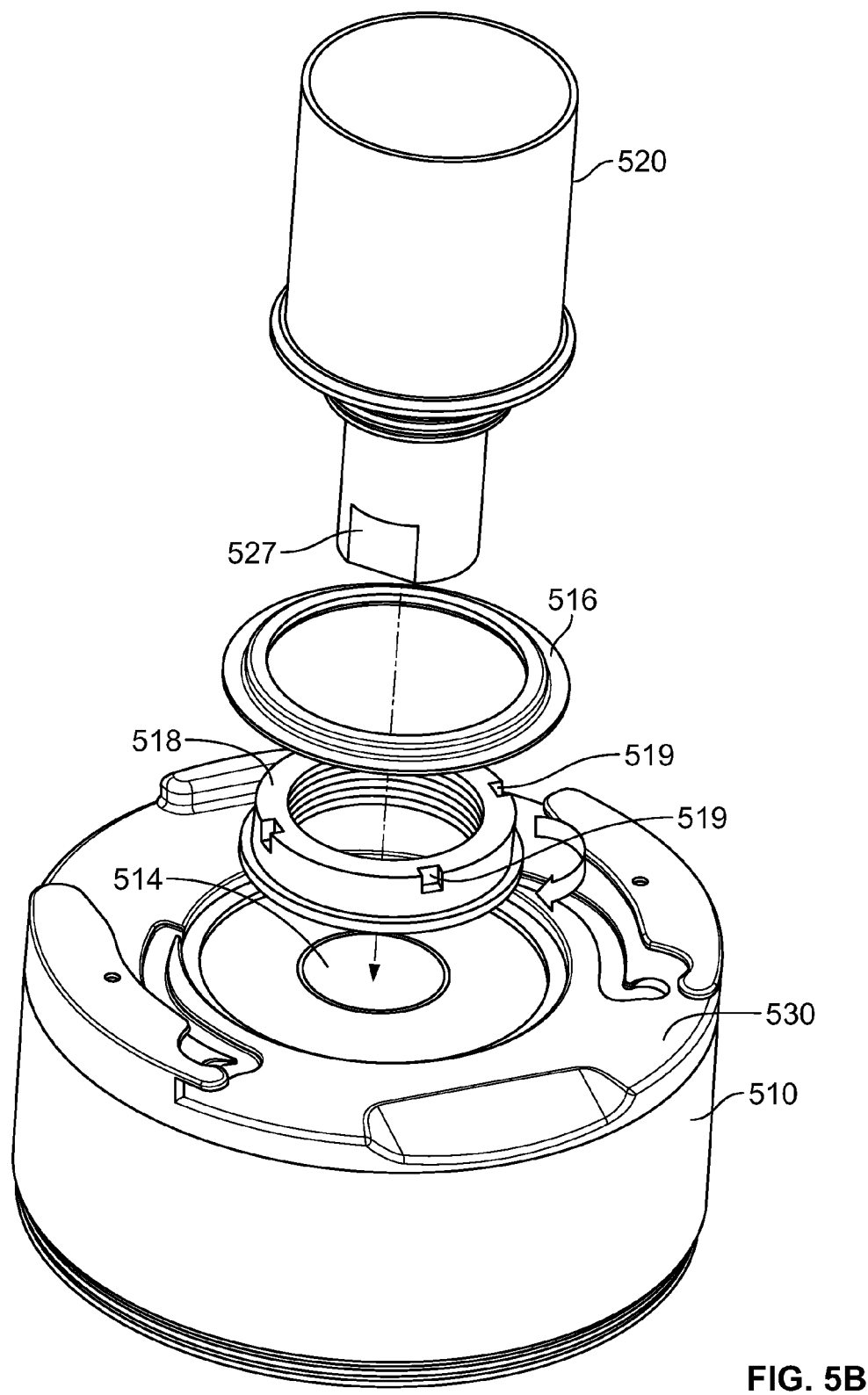

FIGS. 5A and 5B depict a blood pump 500 according to a fourth embodiment having a similar construction to that of the embodiments described above, but having a multi-component coupling feature 512. The coupling feature includes a capture ring 516 and a rotating threaded component 518 that mates with threads 525 in the inflow cannula 520. The capture ring 516 secures the rotating threaded component 518 to the pump cap 530, but allows for the rotating threaded component 518 to freely rotate. The rotating threaded component thus prevents unintentional unthreading of the threaded connection between the rotating threaded component 518 and the inflow cannula 520. The rotating threaded component 518 mitigates the risk of unthreading because torque on the inflow cannula 520 after connection will merely cause the rotating threaded component 518 to rotate with the inflow cannula 520. The rotating treaded component 518 and the capture ring 516 can be arranged to mitigate the risk of opposing torque being placed on the rotating threaded component 518. The capture ring 516 can be welded to the pump cap 530 or the pump housing 510. The capture ring 516 holds the rotating threaded component 518 against the remainder of the pump housing 510. The dimensions of the rotating threaded component 518 can prevent the rotating threaded component 518 from becoming detached from the remainder of the pump housing 510, but dimensions of the rotating threaded component 518 and of the cavity between the pump housing 510 and the capture ring 516 allow the rotating threaded component 518 to freely rotate without excessive frictional or mechanical countering forces. In some embodiments, the rotating threaded component 518 has a circular outer perimeter. The capture ring 516 can have a circular inner surface. The inflow cannula 520 can be threaded into the rotating threaded component until the end of the inflow cannula is seated in the rotor well 550. The rotating threaded component 518 can include grooves 519 to allow the rotating threaded component 518 to be held stationary or be rotated during the threading of the inflow cannula 520 into the rotating threaded component 518. Grooves 519 include one or more surfaces that are generally in a plane including an axis of the threads. The axis of the threads is the axis about which the threads spiral. Surfaces that are in a plane including an axis of the threads can be engaged to control the rotation of the rotating threaded component 518 to allow the inflow cannula 520 to be threaded into the rotating threaded component 518. In other embodiments, grooves 519 can be replaced by notches or ridges also providing a good gripping arrangement. In some embodiments, a tool can be used to engage the grooves 519 during threading (and unthreading) operations.

The end of the inflow cannula 520 shown in FIGS. 5A and 5B include flats 527 to prevent auto-rotation of the inflow cannula. The flats 527 engage with corresponding structures along the flow passage 514 of the pump housing 510 to ensure that the inflow cannula 520 does not rotate relative to the pump housing during use. In some embodiments, the flats are part of a snap-fit connection that can be overcome with a torque greater than a predetermined torque. For example, the predetermined torque can be set at a level greater than the torques normally experienced by a blood pump when implanted.

Figure 6A:
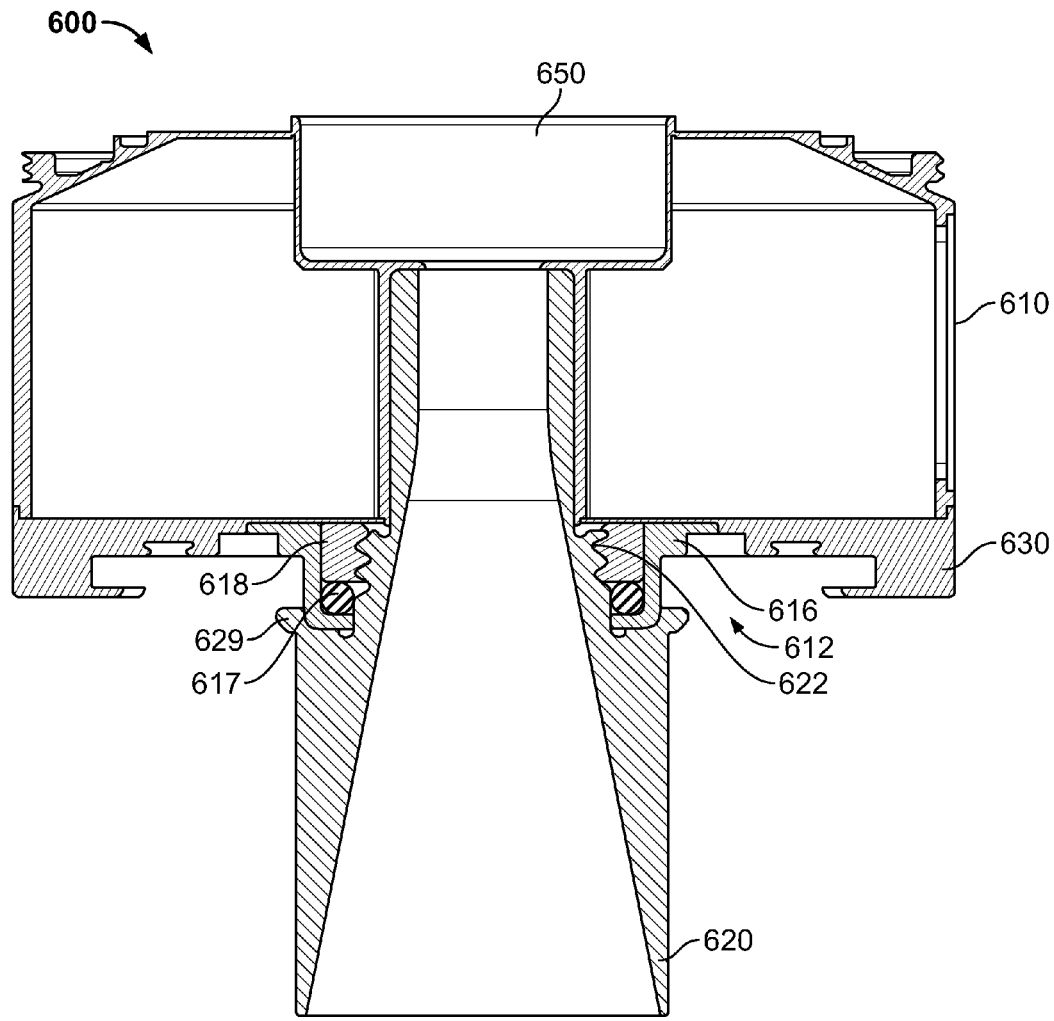
FIGS. 6A and 6B illustrate a second embodiment of an implantable medical pump system having an inflow cannula having a multi-component threaded attachment.
Figure 6B:
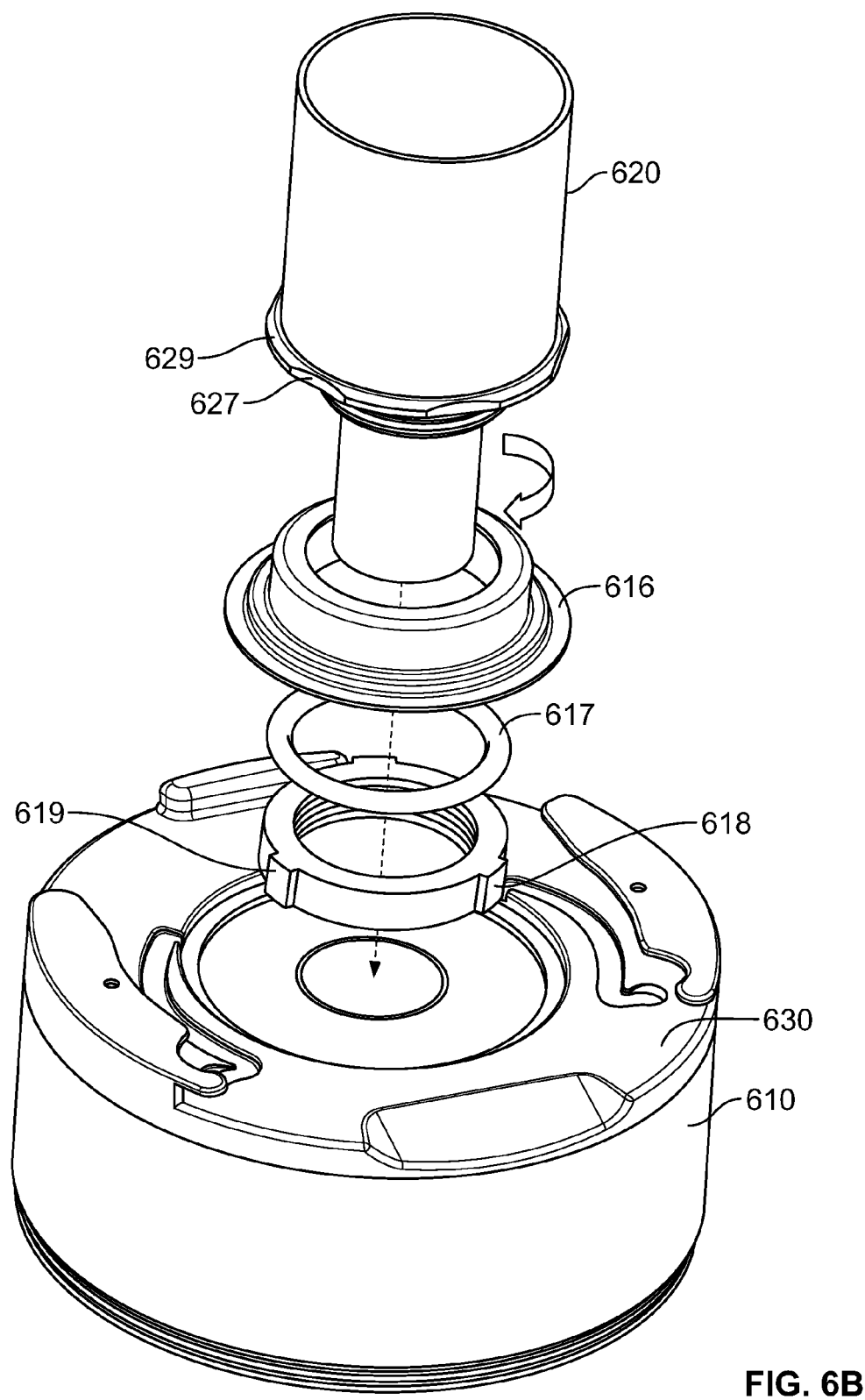

FIGS. 6A and 6B illustrate a blood pump 600 according to a fifth embodiment having a modified multi-component coupling feature 612 including a capture ring 616, a threaded component 618, and an O-ring 617. The O-ring 617 can be pressed between the capture ring 616 and the threaded component 618 to mitigate the risk of blood and/or other fluids leaking past the threaded connection. Threaded component 618 is adapted to mate with threads 622 in the inflow cannula 620. The capture ring 616 secures the threaded component to the pump cap 630. The capture ring 616 can be welded to the pump cap 630 or the pump housing 610. The inflow cannula 620 can be threaded into the threaded component until the end of the inflow cannula is seated in the rotor well 650. The threaded component can include keyways that mate with the capture ring 616 to prevent rotation during assembly. The keyways can include one or more surfaces that are generally in a plane including an axis of the threads. Surfaces that are in a plane including an axis of the threads can be engaged to control the rotation of the threaded component 618 to allow the inflow cannula 620 to be threaded into the threaded component 618. In other embodiments, keyways can be replaced by grooves, notches, or ridges also providing a good gripping arrangement.

FIGS. 6A and 6B illustrate a ridge 629 having grooves 627 therein. Grooved ridge 629 can permit a tool to easily grasp the inflow cannula 620 for installing the inflow cannula to the pump housing 610. Projections 619 can be formed on the threaded component 618 to allow the threaded component 618 to be held stationary or be rotated during the threading of the inflow cannula 620 into the threaded component 618.

Figure 7:
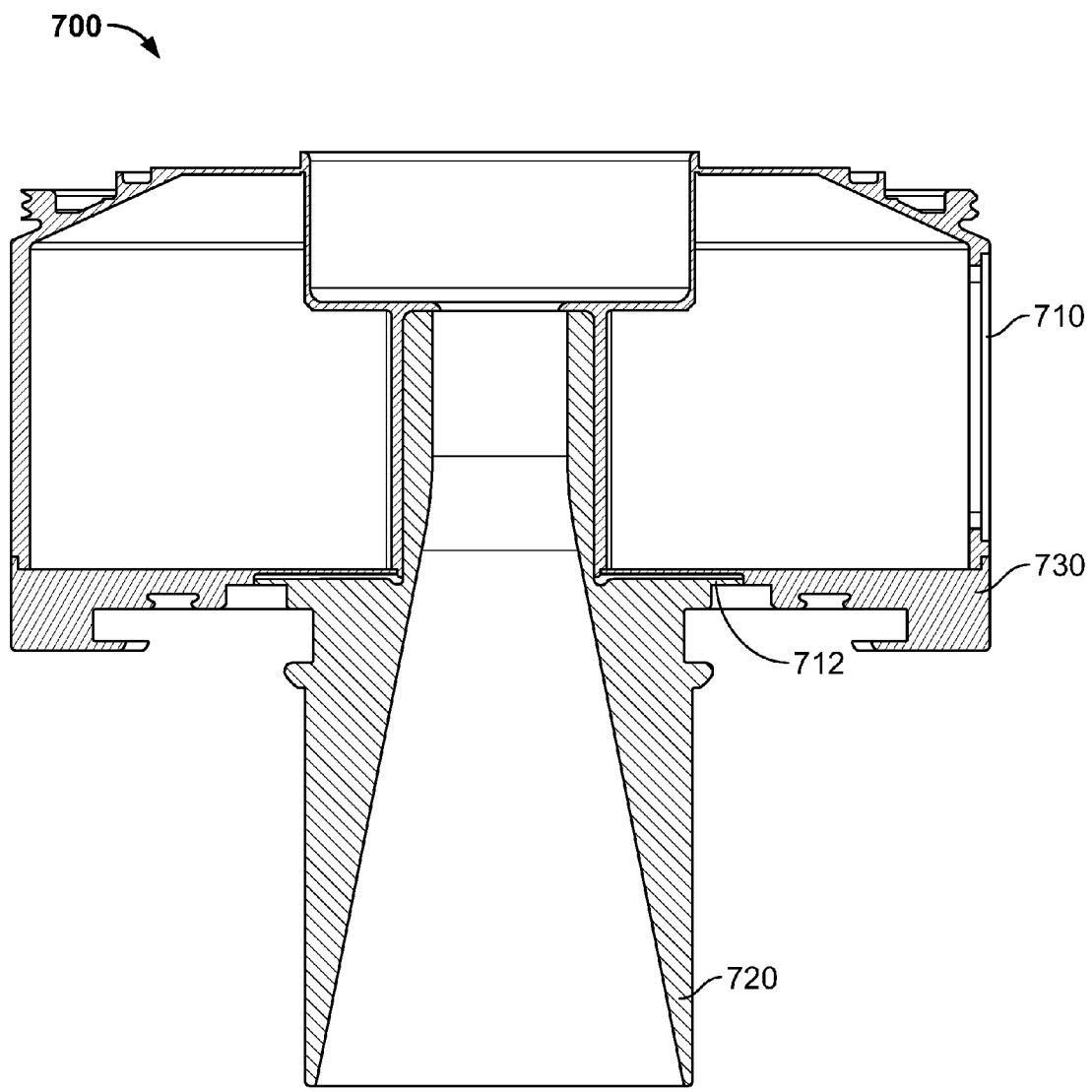
FIG. 7 illustrates an embodiment of an implantable medical pump system having welded connection between an inflow cannula and the pump housing.

FIG. 7 illustrates a blood pump 700 according to a sixth embodiment having an inflow cannula 720 having a flange 712 adapted to be welded to the pump housing 710 or the pump cap 730. A welded connection can provide a permanent attachment. In some embodiments, the inflow cannula can be attached in a manufacturing facility. In other embodiments, the inflow cannula can be welded to the pump housing at the point of use by a clinician.

Textured Surfaces

One or more blood contacting surfaces of the blood pumps described herein can include textured surfaces that may encourage or promote the formation and adherence of a biologic lining. The choice of whether to include a textured surface or a smooth surface on blood-contacting pump components may affect clinical outcomes. In some embodiments, a sintered titanium beaded surface is applied. The sintered titanium bead surface can be used to promote growth of a neointima layer, pseudo-neointima layer, endothelial layer, or combination thereof. A biological layer (e.g. pseudo-neointima) formed on pump surfaces can act similar to a body surface to mitigate thrombus formation. Even in the absence of a biologic layer, the surface can be treated or modified in other ways so it becomes passivated. The lack of a textured surface may be desirable in some circumstances because it is easier to clean.

The textured surfaces may be made from a metal, such as a powdered metal, or a polymer. For example, the textured surface may be a sintered titanium beaded surface. Textured surfaces and their fabrication are known in the art and are used in a variety of medical applications. For example, U.S. Pat. No. 6,050,975 to Poirier, which is hereby incorporated by reference for all purposes, describes textured surfaces. The roughness of the textured surface can be measured by determining a Ra value, which is the arithmetic average of the absolute amplitude values of the surface. In some embodiments, the Ra value of the textured surface is greater than 100 millionths of an inch, greater than 200 millionths of an inch, or greater than 500 millionths of an inch. In some embodiments, the textured surface has a Ra value of at least 200 millionths of an inch, at least 500 millionths of an inch, or at least 1000 millionths of an inch. In some embodiments, the textured surface has a Ra value of less than 10,000 millionths of an inch, less than 5,000 millionths of an inch, less than 1,000 millionths of an inch, or less than 500 millionths of an inch. In some embodiments, the smooth surfaces can have a Ra value of less than 100 millionths of an inch. The pump cover may also include textured blood-contacting surfaces.

Textured surfaces, however, may be difficult to clean after exposure to an unsterile environment and/or wet environment. As discussed below, calibration of a blood pump includes operating the pump prior to implantation using a calibration fluid. Because in some embodiments the inflow cannula includes textured surfaces exposed to the fluid, the pump may require a tedious and time-consuming cleaning process before implantation. There may also be the risk that the surface does not become entirely clean and the pump will not be accurately calibrated when it is implanted. It may also be contaminated from the calibration process.

Figure 8A:
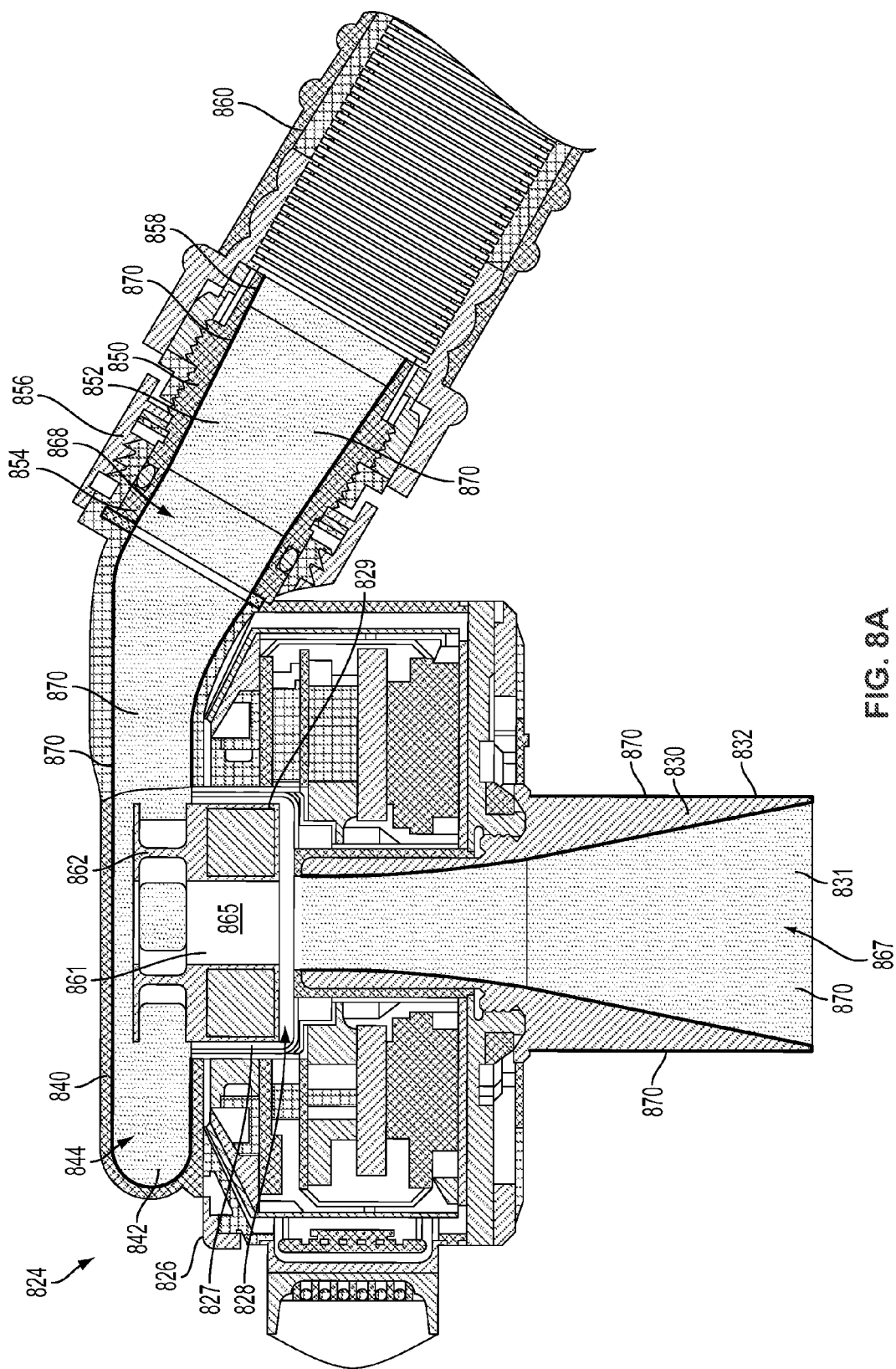
FIG. 8A is a perspective view of a blood pump having textured surfaces.

FIG. 8A illustrates an example of a blood pump 824 having various components with textured surfaces that include a coating 870 of microspheres. In various embodiments, the coating comprises sintered titanium microspheres. The blood pump 824 includes a housing 826 that does not include textured surfaces that contact blood. The blood pump 824 also includes an inflow cannula 830, a pump cover 840, and an outflow adapter 850, each of which is removably attachable to the pump housing 826 and includes one or more textured surfaces having the coating 870. In FIG. 8A, the coating 870 is shown with a dotted pattern and edges having the coating 870 are shown with darkened lines.

Because textured surfaces of the exemplary pump 824 are included on only components that are removable from the housing 826, the removable components can be replaced with production equivalent components having smooth surfaces for the purposes of pump calibration. In this manner, surfaces with the coating 870 are not exposed to contamination during calibration. In the assembled blood pump 824, the majority of the surfaces that contact blood have the coating 870, which limits the potential for thrombus formation. Additionally, this configuration eliminates or reduces the need to clean the textured surfaces exposed during the calibration process. Instead, the components can be replaced with production equivalents without affecting the rest of the pump system. By contrast, conventional pumps require disassembly of the pump to replace similar components. Thus, the exposed components in a conventional setup cannot be replaced without requiring the need to perform another calibration process.

The housing 826 has an inner wall 827 that defines a rotor well 828. A rotor 829 is received in the rotor well 828 and rotates within the rotor well 828 when the blood pump 824 is in use. The inner wall 827 that defines the rotor well 828 is located in the path of blood flow through the pump 824 and thus contacts blood. The inner wall 827 is smooth, for example, the surface of the inner wall 827 does not have the coating 870.

The rotor 829 has blades 862 that extend radially outward from an axis of rotation of the rotor 829. The rotor 829 also includes an inner surface 861 that defines a central opening 865 that permits blood flow through the rotor 829. The inner surface 861 is smooth, for example, without the coating 870. In some implementations, none of the surfaces of the pump housing 826 or the rotor 829 have textured surfaces, such as powdered metal coatings. Because the pump housing 826 and the rotor 829 do not have any powdered metal coatings on blood-contacting surfaces, the pump housing 826 and the rotor 829 may be easily cleaned after use in calibration of the blood pump 824.

As discussed further below with respect to FIGS. 8B-8F, in some implementations, the coating 870 is deposited on most or all blood-contacting surfaces of the inflow cannula 830 and the pump cover 840. As a result, a majority of the blood-contacting surfaces of the pump include the coating 870, even though the housing 826 may be free of the coating 870. For example, because the inflow cannula 830 extends into the pump housing 826, a surface having the coating 870 is located at a position within the housing 826 even though the coating 870 is not deposited on the housing 826.

The blood pump 824 has an inlet 867, defined by the inflow cannula 830, and an outlet 868 defined by the pump cover 840. A blood flow path is defined between the inlet 867 and the outlet 868. Surfaces with the coating 870 occur along the entire blood flow path except in the rotor well 828. For example, surfaces having the coating 870 can occur along all regions of the blood flow path except in regions adjacent the rotor 829, or adjacent blades 862 of the rotor 829.

FIGS. 8B and 8C illustrate the inflow cannula 830, which has an inner surface 831, a first outer surface 832 that extends outward from the blood pump 824, and a second outer surface 833 that is received within the blood pump 824. The coating 870 is deposited on at least a portion of the inner surface 831 and at least a portion of the first outer surface 832, which are blood contacting surfaces. The inflow cannula 830 has a proximal edge 835 that may also include the coating 870, or may not include the coating 870. In some implementations, a portion of the outer surface 832 may omit the coating 870 to avoid undesired interactions with myocardial tissue. In some implementations, all of the surfaces of the inflow cannula 830 that are exposed to blood have the coating 870. In some implementations, the coating 870 is not deposited on the second outer surface 833, which does not contact blood.

In some implementations, the coating 870 is applied to a proximal region 837 of the interior surface 831, but the coating is not applied to a distal region 835 of the interior surface 831. The proximal region 837 includes the portion of the inner surface 831 that extends from the pump housing 826 in the assembled blood pump 824. The proximal region 837 may also extend into the pump housing 826, and may extend along substantially all of a tapered portion of the inner surface 831. The distal region 836 can be a generally cylindrical region that is located adjacent the rotor well 828 in the assembled blood pump 824. In some implementations, the distal region 836 is a region having the smallest inner diameter of the inflow cannula 830. The coating 870 may be omitted along some or all of the distal region 836 to provide a transition region between, for example, the textured surface of the proximal region 837 and a surface of the rotor well 828 having a different texture (e.g., a smooth surface).

Figure 8D:
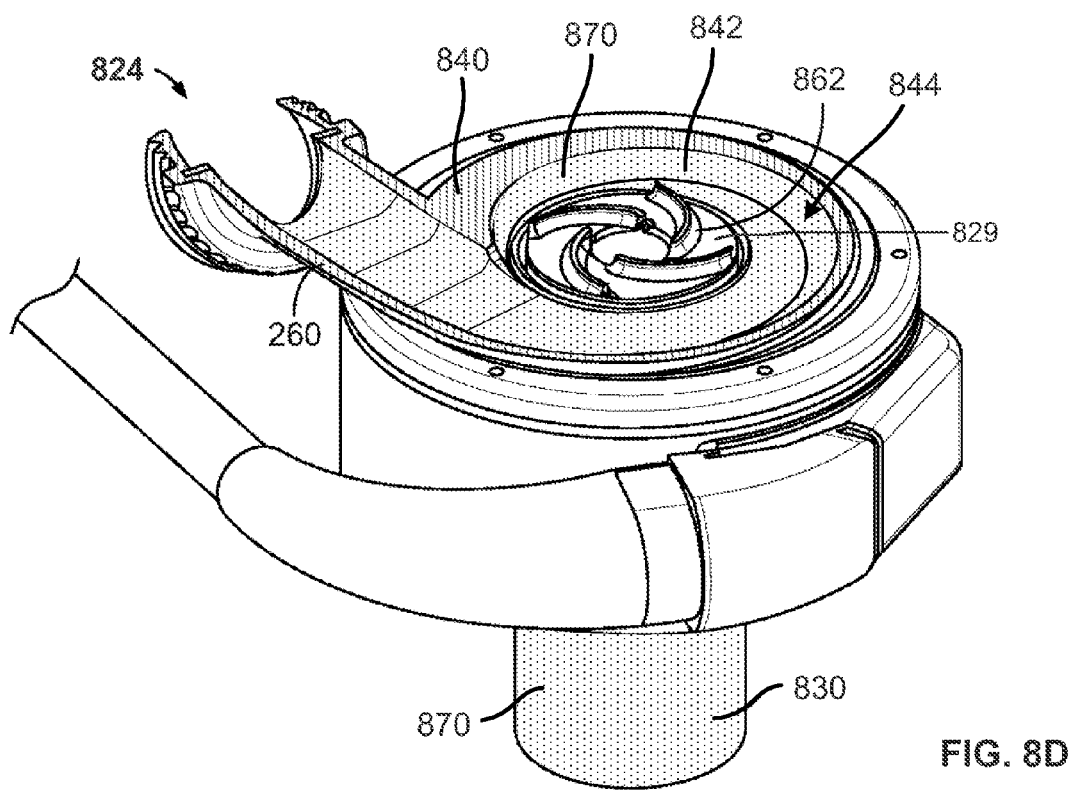
FIGS. 8B and 8C illustrate an inflow cannula of the blood pump of FIG. 8A, and FIGS. 8D to 8F illustrate a pump cover of the blood pump of FIG. 8A.
Figure 8E:
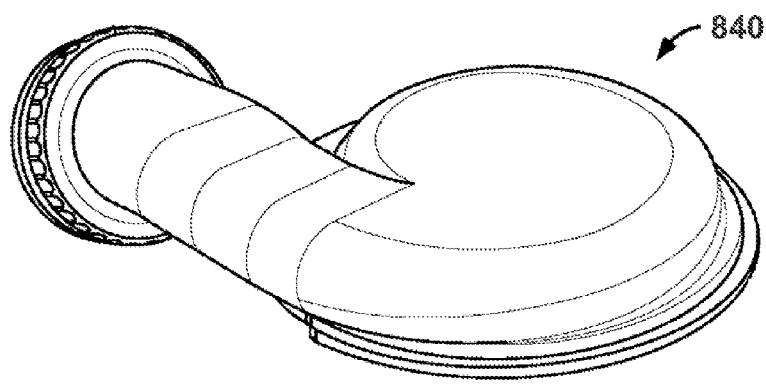
Figure 8F:
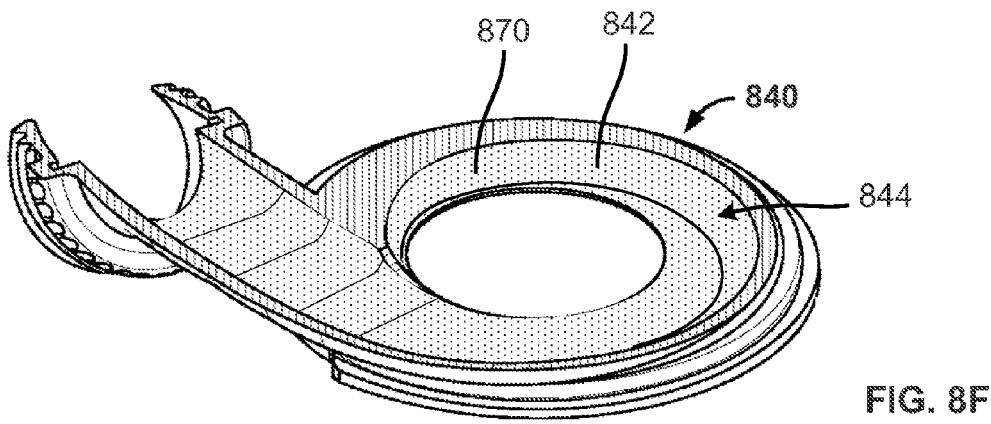

FIGS. 8D to 8F illustrate various views of the pump cover 840. The pump cover 840 has inner surfaces 842 that define a volute 844. The volute 844 can define an expanding volume that converts kinetic energy of blood flow to pressure at an outlet 868 of the blood pump 824. Some or all of the inner surfaces 842 have the coating 870. In some implementations, all of the surfaces of the pump cover 840 that are exposed to blood have the coating 870.

Referring again to FIG. 8A, components other than the pump cover 840 and the inflow cannula 830 can include surfaces with textured surfaces. For example, the outflow adapter 850, which attaches to the pump cover 840, includes the coating 870 on interior surfaces 852 that contact blood. In some implementations, the outflow adapter 850 can be rotatably connected to the pump cover 840. For example, a first end 854 of the outflow adapter 850 can be received within an outlet portion of the pump cover 840 in a non-threaded manner. A fastener 856 can threadedly attach to the exterior threads of the pump cover 840, capturing the first end 854. A second end 858 of the outflow adapter 850 can be attached to an outflow graft 860 that returns blood to a patient's circulatory system. The engagement of the outflow adapter 850 to the pump cover 840 permits the outflow adapter 850, and thus the outflow graft 860, to rotate with respect to the pump cover 840 and the pump 824 as a whole.

Calibration Procedure

A controller assembly and/or a controller in the pump housing 110 can include software that controls the operation of the pump and/or calculates the flow rate of the implantable blood pump system while in service. The controller assembly or the controller in the pump housing can include a processor (e.g., a computer processor) that executes instructions and/or outputs data. Clinicians can use flow rate information, along with other information, to determine the optimal operational characteristics of the pump for each patient. A pre-implantation calibration of this software can be used to ensure that the flow rate calculations are accurate for each particular implantable medical pump. Calibration can improve the accuracy of detecting ventricular suction and/or other clinically relevant events.

Figure 9:
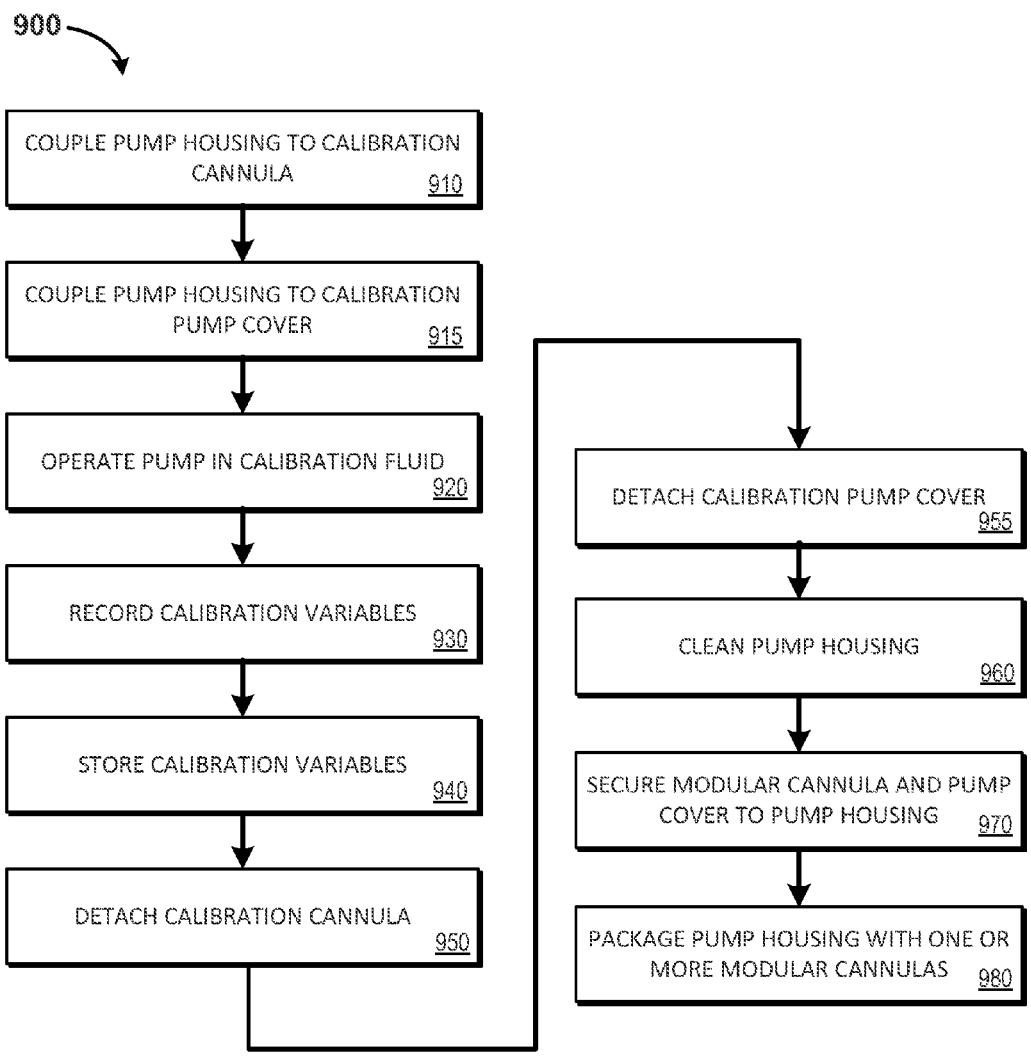
FIG. 9 is a flow chart of a calibration process according to certain embodiments.

FIG. 9 is a flow chart of an exemplary pre-implantation calibration method for an implantable medical pump. In some implementations, components of the medical pump that have a textured surface, such as the coating 870, are not used during calibration to avoid contamination. For purposes of calibration, clinical pump components having textured surfaces are replaced with different components, referred to as calibration components, for use during calibration. The clinical components do not need to be cleaned after calibration because they are detached from the pump and are not used during calibration. In some implementations, where the pump components have textured surfaces, the calibration components have surfaces with a different texture, for example, smooth surfaces. In other implementations, the calibration components have surfaces with the same textures as the clinical pump components.

In the exemplary embodiment, the calibration components are generally production equivalents of the clinical components. As used herein, "production equivalent" refers to components manufactured using the same process, as would be understood by one of skill in the medical field, and in various respects, the field of medical device manufacturing. Very generally, the calibration components are manufactured to the same specifications and are functionally equivalent to the clinical components. Thus, the calibration process does not need to be repeated when the calibration components and clinical components are switched. The hydraulic operation of the pump is the same during calibration as in the final clinical configuration of the pump. For example, the fluid pathway defined by a calibration cannula, a calibration cover, and the pump housing has the same geometry as the fluid pathway defined by the clinical inflow cannula, the clinical pump cover, and the pump housing. In addition, the particular motor and particular rotor used together for calibration are shipped and implanted together. As a result, with the calibration components attached to the housing, the flow geometry through the pump in the calibration assembly is the same as the flow geometry through the pump in an assembly of the pump with clinical components.

For example, the portions of the calibration components that define portions of a blood flow path within the medical pump can have substantially equal dimensions to the corresponding portions of clinical components. With the calibration components, the medical pump can have performance characteristics that are within a predetermined tolerance of characteristics of the medical pump with clinical components used for implantation. For example, performance of the medical pump with the calibration components may deviate from the performance of the blood pump with the clinical components by 20% or less, 10% or less, or 5% or less. Dimensions of the calibration components may be, for example, 10% or less or 5% or less of the dimensions of clinical components.

The calibration components can be production equivalents of the clinical components. In other words, the calibration components are manufactured using the same production procedures and under the same protocols used to manufacture the clinical components. In some implementations, the calibration components are manufactured to the same specifications as the clinical components.

The method 900 includes coupling 910 a pump housing (including the motor) to a calibration cannula prior to operating the motor with the calibration fluid. The calibration cannula can be reusable and used for multiple calibration processes with multiple pump housings. The calibration cannula can have dimensions equal to or approximating that of an inflow cannula (such as those shown in the figures). For example, the calibration cannula can have the same features and dimensions of an inflow cannula for the pump, but with smooth surfaces instead of textured surfaces. As an alternative, the calibration cannula can have textured surfaces. For example, the calibration cannula can be a second inflow cannula that is identical to the inflow cannula of the pump.

When a pump cover includes textured surfaces, the method 900 also includes coupling 915 the pump housing to a calibration cover, which can have dimensions equal to or approximating that of the pump cover. It is possible that the difference between the calibration cover and the pump cover is only a difference in surface texture, with the pump cover having a textured surface and the calibration cover having a corresponding surface that is smooth. Even in this case, the inaccuracies during the calibration process may still remain within acceptable levels. As an alternative, the calibration cover may include textured surface. For example, the calibration cover may be a second pump cover that is identical to the pump cover.

In other embodiments, the calibration can occur when the pump housing is connected to the pump cover. For example, in some embodiments, the pump cover can be free of textured surfaces and thus mitigate the risk of contamination due to the calibration procedure.

After connecting the calibration cannula and the calibration cover to the pump housing, the motor is operated 920 using a calibration fluid. Calibration variables are recorded 930. The calibration values can be based on a flow, a pressure, a speed, an operational power, or a combination thereof of calibration fluid pumped by the blood pump. Recorded calibration variables are then imbedded 940 in the software of a control system of the pump. For example, the calibration variables may be stored in an internal memory of the pump. As another example, the calibration variables may be stored in a memory of an implantable controller or an external controller. During operation of the pump, the values stored as calibration variables may be accessed and used to control operation of the pump.

The pump housing (including the motor) is then detached 950 from the calibration cannula. A calibration cover can also be detached 955. Exposed surfaces of the pump housing are then cleaned 960. Cleaning 960, for example, can include the use of soaps, detergents, water, organic solvents, heat, pressure, and/or ultrasonic energy.

After cleaning, an inflow cannula can be secured 970 to an attachment feature of the pump housing. A pump cover can also be secured to the pump housing. In some embodiments, the inflow cannula and/or the pump cover are secured to the pump housing prior to packaging. In other embodiments, the inflow cannula and/or the pump cover are secured to the pump housing at the point of use by a clinician. In some embodiments, the calibrated blood pump is packaged 980 with one or more inflow cannulas. The packaging can further include tools adapted to secure the inflow cannula to the pump housing.

As noted above, the inflow cannula and/or the pump covering can have textured surfaces. The textured surfaces may be difficult to clean following a calibration process. Accordingly, the above noted calibration process results in a calibrated blood pump having textured blood-contacting surfaces while avoiding a contamination risk of the textured surfaces.

Each of the calibration components has features that correspond to the features of the actual pump components. For example, the inflow cannula and the calibration cannula each define a lumen. The pump cover and the calibration cover each have an inner surface that defines a volute. In regions where the pump cover and inflow cannula have textured surfaces, such as a powdered metal coating, the calibration cover and calibration cannula have smooth surfaces.

The calibration components used during the calibration process can approximate one or more of the dimensions of the actual pump components. To approximate a pump component, a calibration component may have one or more dimensions substantially equal to the dimensions of the pump component. For example, the calibration component may have inner dimensions, or dimensions of blood-contacting surfaces, that are within 20%, within 10%, or within 5% of the corresponding dimensions of the pump component. In some implementations, a calibration component is identical to a pump component except for surface texture.

Referring to FIGS. 10A-10G, an inflow cannula can be attached to a pump housing using one or more tools. For example, an inflow cannula 120 can be attached to a pump housing 110 using a specialized socket 1000 and a torque wrench 1010. The torque wrench 1010 can be a torque-measuring wrench. For example, the torque wrench 1010 can include a gauge 1015 that indicates the amount of torque being applied with the wrench 1010. Digital torque wrenches can also be used. The torque wrench 1010 can be used to ensure that the inflow cannula 120 is secured to the pump housing 110 with a predetermined amount of torque. In some embodiments, the predetermined amount of torque is greater than 25 inch-pounds (in-lbf). In some embodiments, the predetermined amount of torque is between 25 and 150 in-lbf. In some embodiments, the torque wrench 1010 is a torque-limiting wrench that limits an amount of torque applied with the wrench to a predetermined amount.

The socket 1000 has a cylindrical inside surface 1028 having dimensions that correspond to the outside surface of the inflow cannula 120. The socket 1000 also includes grooves or projections that correspond to features of the inflow cannula 120 so that the socket can be used to apply torque to the inflow cannula 120 about a central longitudinal axis 1050 (illustrated in FIGS. 10E and 10F). FIGS. 10A-10G illustrate a socket 1000 having projections 1027 extending out from a rim of the socket 1020 in a direction that is generally parallel with the central longitudinal axis 1050. In certain embodiments, the socket 1000 can include grooves or projections on an inside surface 1028 of the socket that mate with corresponding features of an inflow cannula. A socket 1000 and/or a torque wrench 1010 can be supplied with one or more cannulas and one or more blood pumps as part of a kit and/or sold separately. In some embodiments not shown, the socket 1000 can be integral with a torque wrench 1010. The torque wrench 1010 can be programmed to identify a predetermined amount of torque.

Referring to FIGS. 10G to 10M, the pump cover 160 can also be attached to the pump housing 110 or adjusted relative to the pump housing 110. The pump 105 can include a capture ring 130 that has an inner diameter that is smaller than an outer diameter of the pump cover 160. The capture ring 130 fits over a peripheral edge 140 of the pump cover 160, and when attached to the pump housing 110, the capture ring 130 captures the pump cover 160 against the pump housing 110. A sealing ring 162 can be located between the pump cover 160 and the pump housing 110 to limit or prevent blood leakage.

Figure 10A:
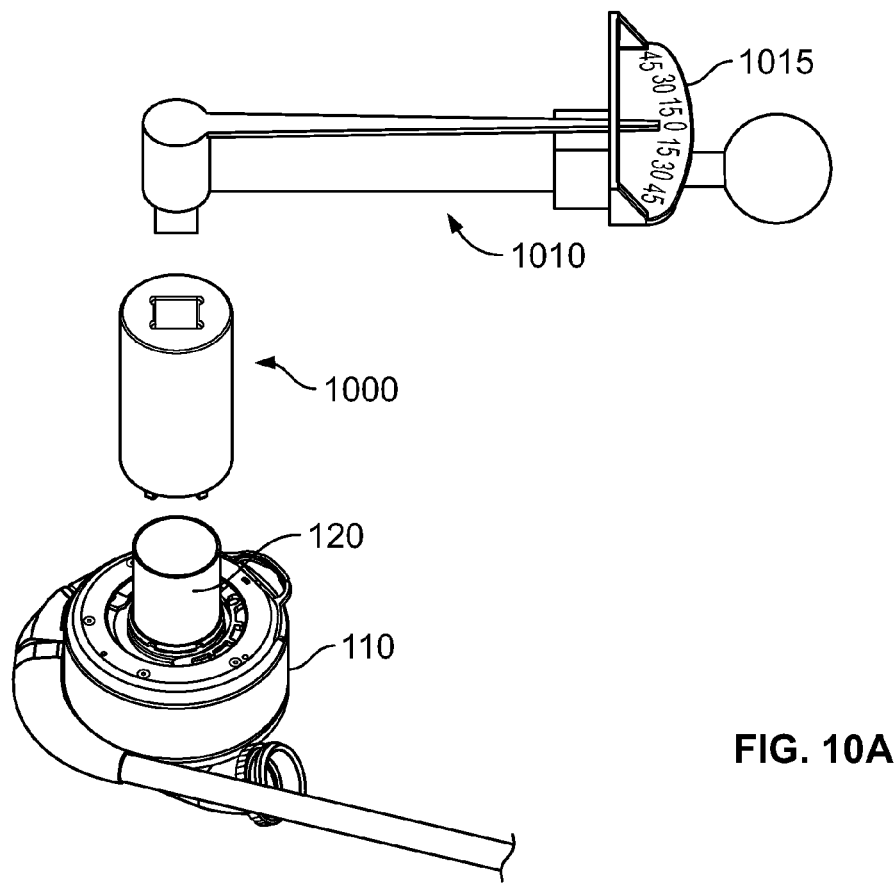
FIGS. 10A-10G illustrate a tool being used to secure an inflow cannula to a pump housing.
Figure 10B:
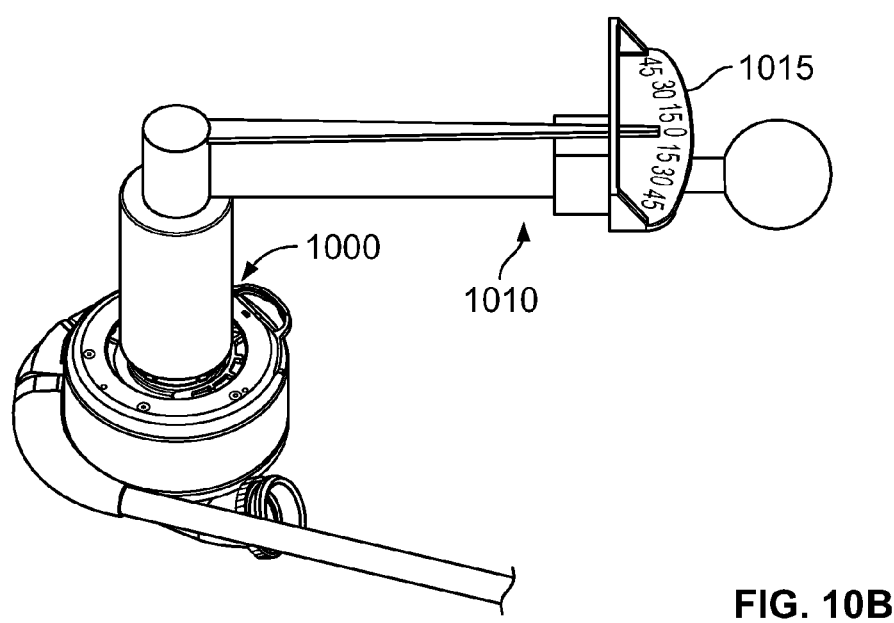
Figure 10C:
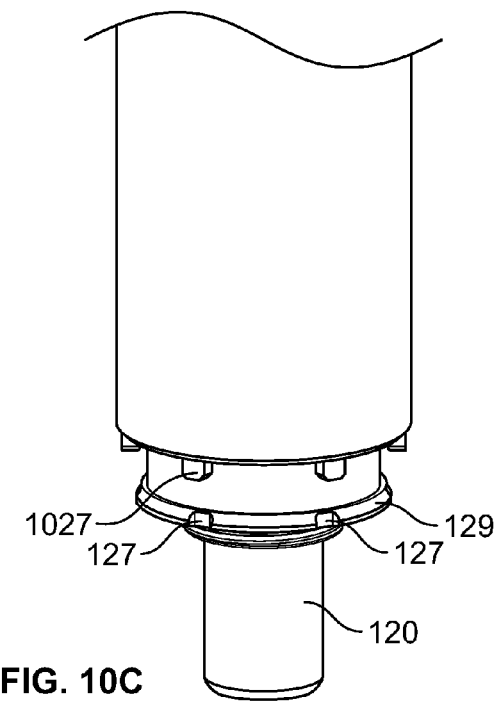
Figure 10D:
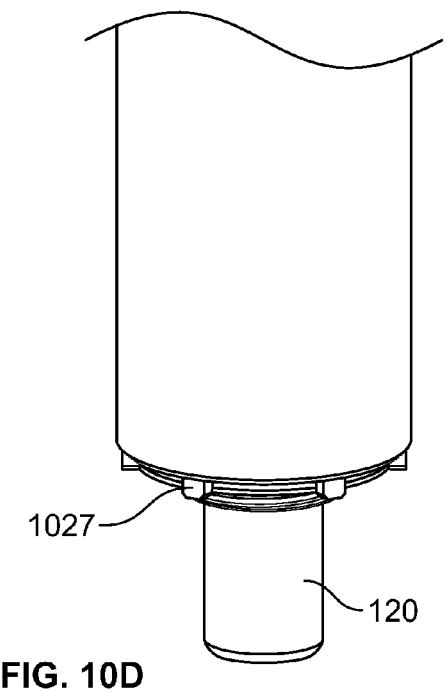
Figure 10E:
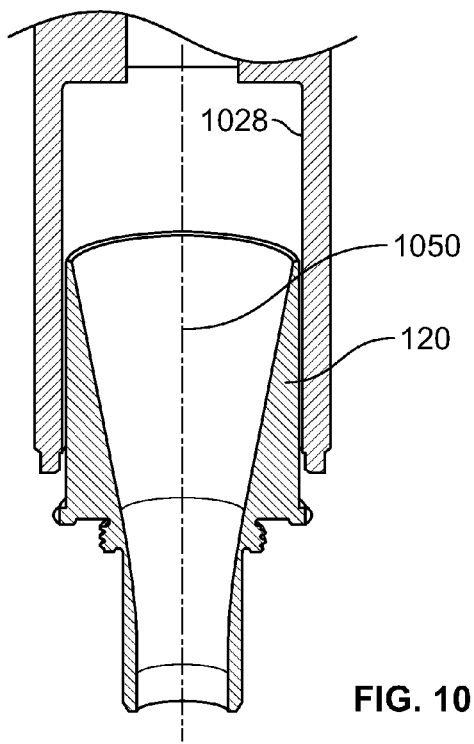
Figure 10F:
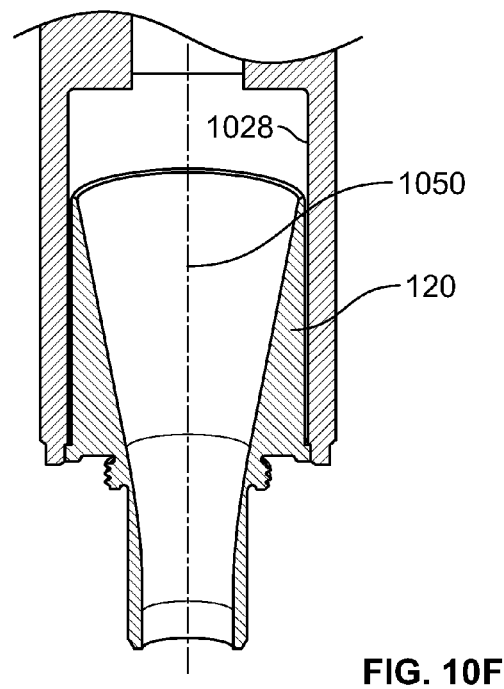
Figure 10G:
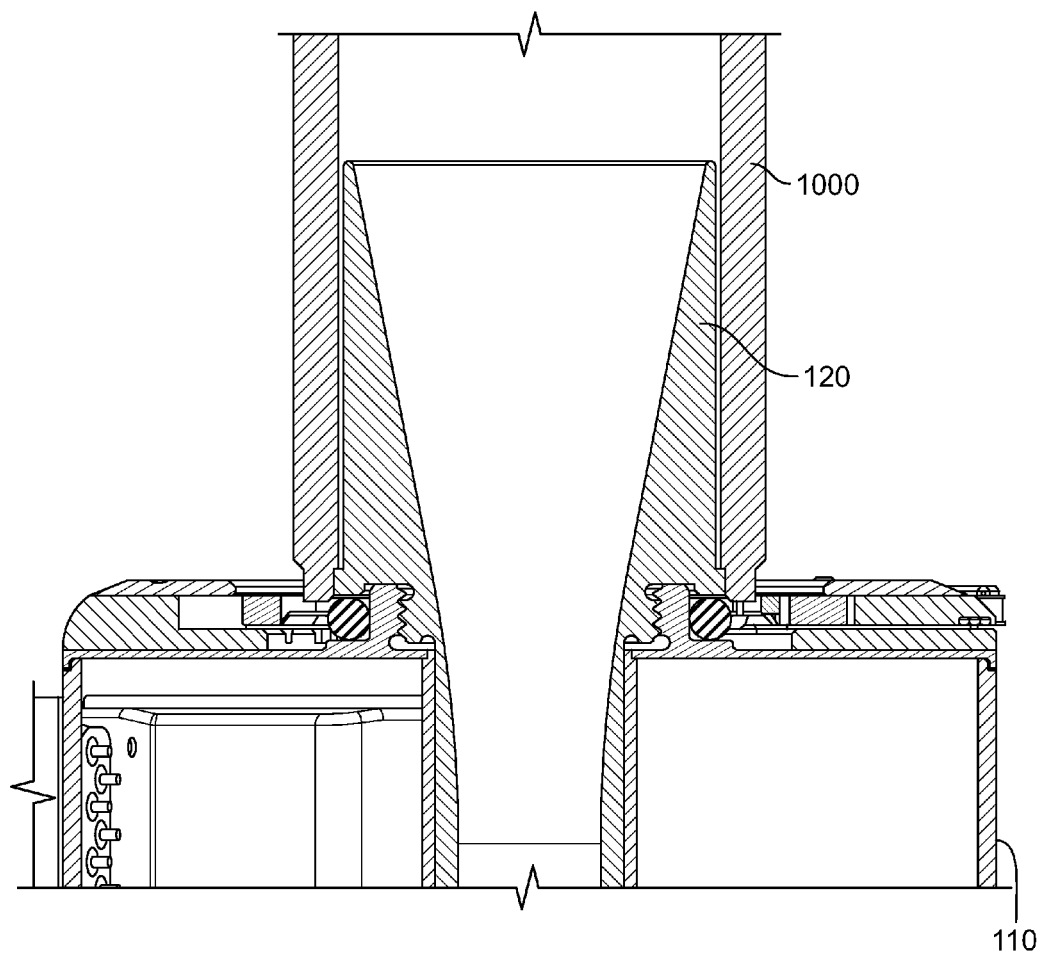
Figures 10H, 10I:
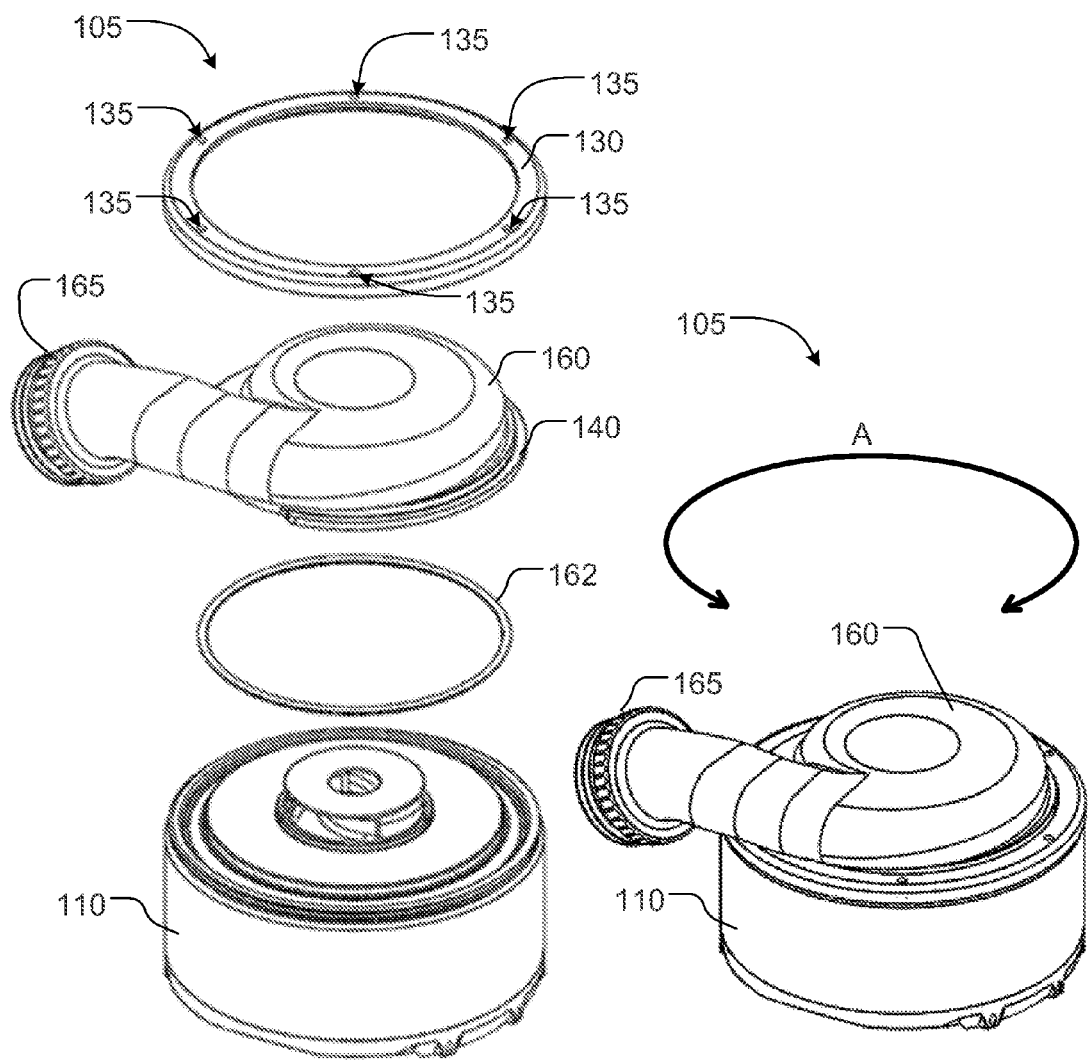
Figure 10M:
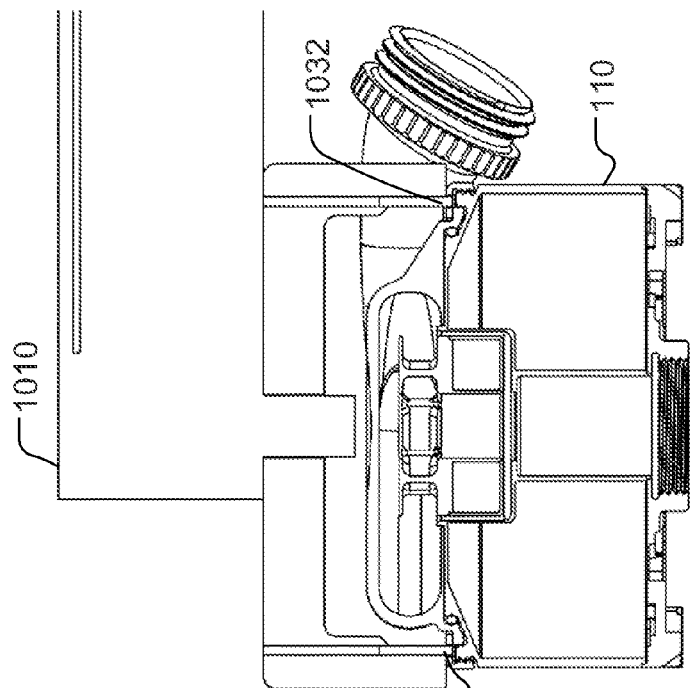

The pump cover 160 engages the pump housing 110 with a non-threaded connection. In some implementations, the pump cover 160 is rotatable relative to the pump housing 110 while secured to the pump housing 110, for example, while the pump cover 160 is captured between the pump housing 110 and the capture ring 130. When assembled, the pump cover 160 and the capture ring 130 maintain the pump cover 160 in a fixed position, due to friction and in some implementations, compressive force, unless at least a predetermined amount of torque is applied. When sufficient torque is applied to the pump cover 160 relative to the pump housing 110, the pump cover 160 may rotate in a direction shown by arrow A (FIG. 10I). In some implementations, the pump cover 160 rotates relative to the pump housing 110 about a central axis of the pump 105, such as a central longitudinal axis through the inflow conduit 120 or an axis of rotation of a rotor.

In some implementations, a clinician first applies torque to loosen the capture ring 130 from the pump housing 110, which permits the pump cover 160 to rotate. When the outflow port 165 is in a desired orientation, the clinician tightens the capture ring 130 to restrict further rotation of the pump cover 160.

In some implementations, a clinician can rotate the pump cover 160 with respect to the pump housing 110 without loosening the capture ring 130. The pump cover 160, pump housing 110, and capture ring 130 may be dimensioned to permit rotation of the pump cover 160 while the capture ring 130 is fully secured to the pump housing 110. In some implementations, to facilitate rotation, a coating or insert, such as a polytetrafluoroethylene ring, can be inserted between the pump cover 160 and the capture ring 130 and/or between the pump cover 160 and the pump housing 110. As a result, a clinician receiving the assembled blood pump 105 may adjust the position of the outflow port 165 with respect to the pump housing 110 while the pump cover 160 is secured in an implantable configuration.

In some embodiments, the predetermined amount of torque required to loosen the capture ring 130 or rotate the pump cover 160 is greater than 25 in-lbf. In some embodiments, the predetermined amount of torque is between 25 and 150 in-lbf.

Figure 10L:
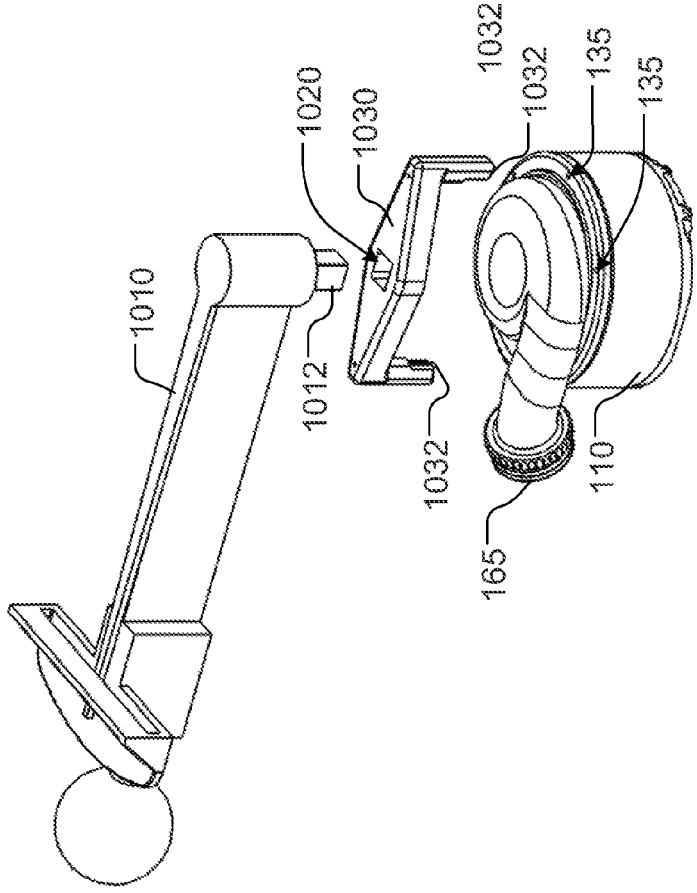

As shown in FIGS. 10J and 10K, the capture ring 130 has interior threads 132 that engage exterior threads 112 defined at an outer perimeter of the pump housing 110. The pump housing 110 also defines a generally circumferential groove 113 that receives the peripheral edge 140 of the pump cover 160 (FIG. 10K). In the assembled pump 105, the peripheral edge 140 is located in the circumferential groove, and an annular wall 134 of the capture ring 130 limits the pump cover 160 from separating from the pump housing 110. Referring to FIG. 10L, a clinician can adjust the position of the outflow port 165 using the torque wrench 1010 or another tool. In the example shown, the torque wrench 1010 engages an adapter 1030 that has a socket 1020 complementary to an extension 1012 of the torque wrench 1010. The adapter 1030 includes pins 1032 that extend into holes 135 defined in the capture ring 130 to establish a secure connection between the adapter 1030 and the capture ring 130. While the pump housing 110 is held in a fixed position, the clinician can use the torque wrench 1010 to loosen the capture ring 130. With the capture ring 130 loosened, the clinician can then rotate the pump cover 160 relative to the pump housing 110. After the pump cover 160 is in a desired rotational orientation with respect to the pump housing 110, the clinician uses the torque wrench to tighten the capture ring 130, fixing the rotational position of the pump cover 160.

In some implementations, the clinician removes the capture ring 130 from the pump housing 110 and replaces the pump cover 160 with a different pump cover, for example, a pump cover with an outlet having a size or trajectory different from the outflow port 165. The clinician then replaces the capture ring 130 to secure the new pump cover to the pump housing 110.

In some implementations, as noted above, the clinician can rotate the pump cover 160 relative to the pump housing 110 without first loosening the capture ring 130 from the motor housing.

Implanted System

Figure 1C:
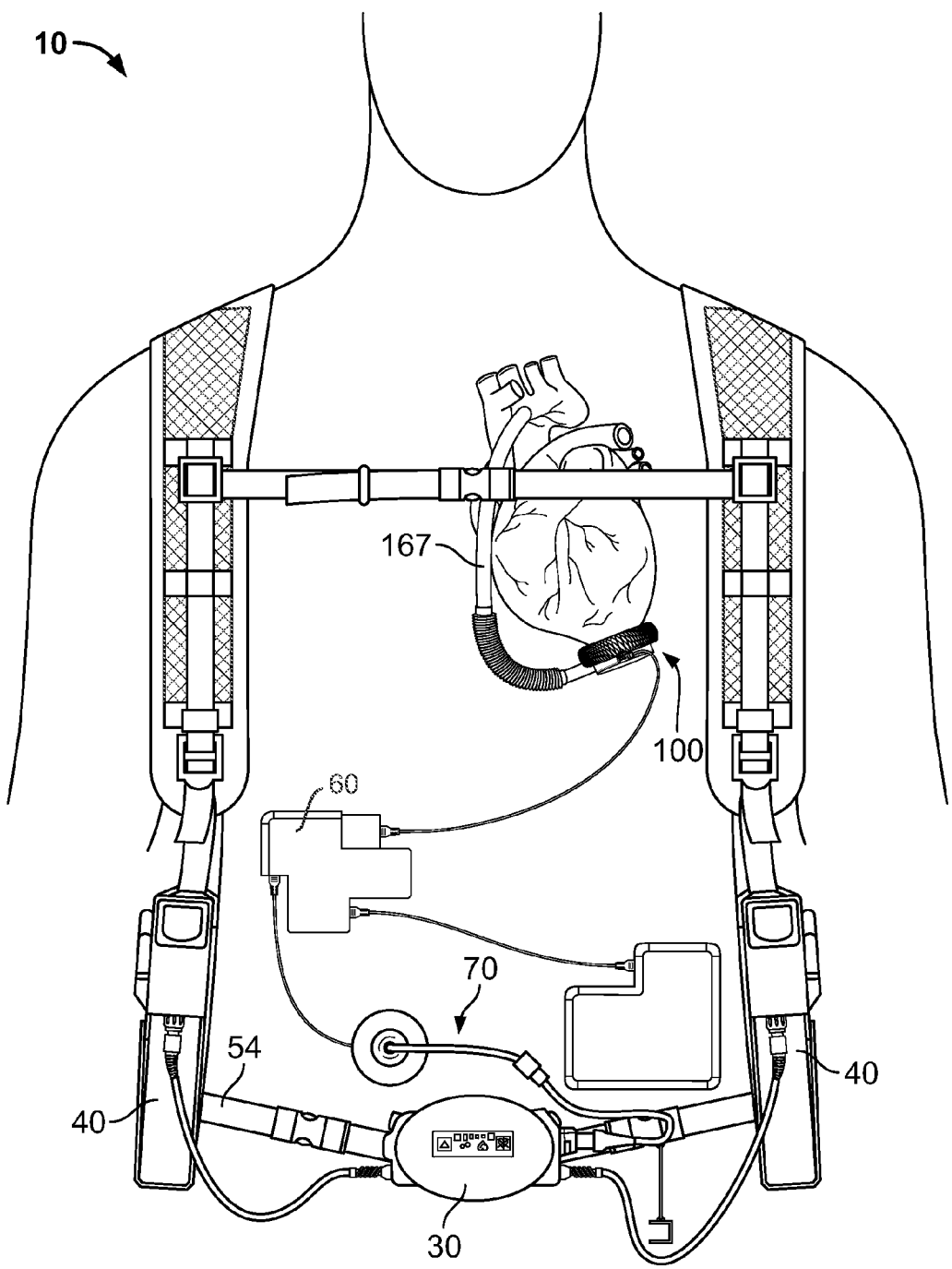
FIG. 1C illustrates an overall system including the implantable medical pump of FIG. 1B.

FIG. 1C is a front view depicting an embodiment of an implantable medical pump system 10 including a portable external controller 30 and two external batteries 40. In the embodiment depicted here, the implanted medical pump system 10 includes an implantable medical pump 100, an internal controller assembly 60 (that can include one or more internal batteries), and a percutaneous lead 70. The controller assembly 60 can be implanted in, for example, the thorax, the abdomen, or any other part of a patient's body as appropriate and can be electrically connected to the implantable medical pump 100 such that the controller assembly 60 can control functions of and monitor the implantable medical pump 100. As discussed below, the controller assembly 60 can include software (e.g., machine-readable instructions that may be executed by one or more processors) and stored calibration values for calculating flow rates and/or controlling the operation of the implantable medical pump 100. In other embodiments (not shown), a controller storing software and calibration values can be included within the pump housing 110 rather than in a separate housing.

The use of the controllers 30, 60 between the pump 100 and the external batteries 40 is optional. For example, control of the pump 100 can be implemented in the pump 100, and the external controller 30 and implanted controller 60 may be omitted. As an alternative, the controller may be implemented entirely in the controller 30 or in the implanted controller 60.

Power for normal operation of the system 10 can be supplied by the internal batteries included in the controller assembly 60, within the pump housing 110, or by an external power source (such as the external batteries 40). The blood pump system 10 can be electrically coupled via the percutaneous lead 70 to an external controller and/or power source. The percutaneous lead 70 can include a flexible outer housing enclosing redundant electrical lead sets, for example as discussed in U.S. patent application Ser. No. 12/472,812, filed May 27, 2009, which is hereby incorporated by reference for all purposes. Other systems including blood pumps are also contemplated.

Referring back to FIGS. 1A and 1B, the implantable medical pump 100 can also include an outflow port 165 for expelling blood that has been drawn by the implantable medical pump 100 from the interior chamber of the heart. As shown, the outflow port 165 can be located along the perimeter of the pump housing 110. In some embodiments, the outflow port 165 can be part of a pump cover 160. The outflow port 165 can be fluidly connected via flexible conduit 167 (see FIG. 1C) to the aorta such that blood drawn from the interior chamber of the heart can be expelled under pressure into the circulatory system of the user. As such, the implantable medical pump 100 can augment the pumping of blood performed by the heart. The implantable medical pump 100 can also include a fluid-tight bulkhead fitting 180 that allows an electrical conduit 185 to pass from outside the implantable medical pump 100 into the interior of the implantable medical pump 100, while maintaining a fluid-tight seal.

Pump housing 110 can define a passage containing a rotor that is actuated by elements at least partially contained within the pump housing 110. For example, the pump housing 110 can include electrical coils. Electrical power can be supplied to the push magnets embedded in the rotor with an electromagnetic field. An example of the motor is described in more detail in co-pending U.S. patent application Ser. No. 13/212,813, filed Aug. 18, 2011, entitled "IMPLANTABLE BLOOD PUMP," which is hereby incorporated by reference for all purposes.

A controller (either inside the pump housing 110 or exterior to the pump housing) can control the delivery of electrical power supplied to the coils to control the flow, speed, or pressure of blood pumped. The rotor can contain hydrodynamic elements, e.g. blades, which functions as an impeller that, when rotating, can increase the pressure of fluid within the implantable medical pump 100. The passage can define a rotor well containing the rotor. Blood can enter through the inflow cannula 120, pass into the rotor well, and be accelerated by the rotor in the rotor well, causing the accelerated blood to flow radially outward and exit through the outflow port 165 where it continues through the flexible conduit 167 and into the circulatory system. The depicted implantable medical pump 100 is advantageously compact and, due in part to the overall mushroom shape, can be readily secured to a heart wall.

FIG. 1B also illustrates an example of how an implantable medical pump can be secured to a heart. The implantable medical pump 100 (e.g., an implanted centrifugal blood pump) can be secured to a heart 20 using a mounting cuff 102 and medical sutures 104 such that an inflow cannula 120 traverses a myocardium of the heart 20.

Implantation Procedure

The blood pump can be implanted in the wall of the left ventricle, e.g., near the apex of the heart. In other embodiments, the implantable medical pump 100 is implanted in the wall of the right ventricle. In other embodiments, the blood pump is attached to an atrium, e.g. if a left ventricle has been resected. The selected implantation site can impact the selected inflow cannula given the variations in myocardial wall thicknesses and shapes, and the desired inflow cannula flow trajectories.

A scalpel and/or a coring knife can be used to incise a cylindrical opening through the apex into the left ventricle approximately the diameter of the exterior end of the inflow cannula. When the opening has been incised, the inflow cannula can be advanced into the opening until the pump housing 210 contacts the heart wall. The blood pump can then be secured in place using sutures and a mounting cuff. The mounting cuff can be attached to the blood pump and/or the myocardium by threads, detents, a series of sutures, a series of snaps, a band or strap, a friction fit, and the like.

A number of embodiments have been described. Nevertheless, it will be understood that various modifications may be made without departing from the spirit and scope of this document. Accordingly, other embodiments are within the scope of the following claims.

What is claimed is:

1. An implantable medical pump system, comprising:
a centrifugal blood pump comprising a pump housing defining a passage therethrough and a rotor within the passage, the pump housing at least partially containing one or more elements configured to actuate the rotor to drive fluid through the passage, the pump housing comprising at least one coupling feature; and
a plurality of differing inflow cannulas, each inflow cannula of the plurality defining a lumen therethrough and being configured for alternate modular attachment to the at least one coupling feature.

2. The system of claim 1, wherein at least one inflow cannula of the plurality comprises a textured blood-contacting surface, and wherein at least a portion of each inflow cannula of the plurality extends into the passage when the inflow cannula is attached to the at least one coupling feature.

3. The system of claim 2, wherein the textured blood-contacting surface comprises sintered titanium powder.

4. The system of claim 1, wherein substantially all of the blood-contacting surfaces of the at least one inflow cannula include a textured coating.

5. The system of claim 1, wherein each inflow cannula of the plurality is configured to extend out from the pump housing when coupled to the at least one coupling feature such that a portion of each inflow cannula of the plurality is configured to traverse an myocardium of a heart.

6. The system of claim 1, wherein the inflow cannula comprises:
   a first portion having a length sufficient to traverse a heart wall, the lumen extending through the first portion;
   an exterior thread pattern to mate with an interior thread pattern of the blood pump, the first portion protruding from the blood pump when the exterior thread pattern engages the interior thread pattern of the blood pump; and
   a second portion having a generally cylindrical outer surface received inside the passage of the blood pump when the exterior thread pattern engages the interior thread pattern of the blood pump, the second portion having a smaller outer diameter than the first portion.

7. The system of claim 1, wherein the inflow cannula is configured to extend along at least 50% of the length of the passage when mechanically coupled to the at least one coupling feature to a rotor well defined by the passage.

8. The system of claim 1, wherein the passage defines a rotor well that receives the rotor, wherein the inflow cannula is configured to extend to the rotor well when mechanically coupled to the at least one coupling feature.

9. The system of claim 1, wherein the system comprises multiple inflow cannulas each configured to be reversibly mechanically coupled to the at least one coupling feature such that at least a portion of the flow cannula extends into the passage, at least two of the inflow cannulas having different lengths.

10. The system of claim 9, wherein at least a first inflow cannula is configured for traversing the myocardium of a left ventricle and a second inflow cannula is configured for traversing the myocardium of a right ventricle.

11. The system of claim 1, further comprising a pump cover that is removably attachable to the pump housing, the pump cover defining a volute and comprising a textured blood-contacting surface.

12. The system of claim 1, wherein the centrifugal blood pump is configured to mount to or directly adjacent to a wall of the heart such that the inflow cannula traverses the heart wall when the system is implanted.

13. The system of claim 1, further comprising:
   a wrench system including a torque-limiting or torque-measuring wrench to facilitate secure attachment of a selected inflow cannula of the plurality with a predetermined amount of torque.

14. An implantable medical pump system, comprising:
   a centrifugal pump housing defining a passage therethrough and a rotor at least partially disposed in the passage in a rotor well, the pump housing at least partially containing one or more elements configured to actuate the rotor to drive fluid through the passage; and
   an inflow cannula that is removably attachable to the pump housing by at least one coupling feature of the housing, the inflow cannula having a lumen defined through the inflow cannula that extends to the rotor well when the inflow cannula is attached to the pump housing by the at the least one coupling feature, the inner surface of the lumen having a textured blood-contacting surface.

15. The implantable medical pump system of claim 14, wherein the lumen of each inflow cannula of the plurality extends into the passage beyond the at least one coupling feature when the inflow cannula is attached to the pump housing.

16. The implantable medical pump system of claim 14, wherein the textured blood-contacting surfaces comprise a powdered metal coating, and the pump housing does not have any blood-contacting surfaces that comprise a powdered metal coating.

17. The implantable medical pump system of claim 16, wherein the powdered metal coating comprises a sintered titanium powder.

18. The implantable medical pump system of claim 14,
   a pump cover removably attachable to the pump housing, the pump cover having an inner surface that defines a volute, the inner surface of the pump cover having a textured blood-contacting surface,
   wherein the inflow cannula, the pump housing, and the pump cover define a blood flow path through the pump, and the pump housing defines a rotor well that receives a portion of the rotor,
   wherein textured blood-contacting surfaces are disposed along the entire blood flow path except the rotor well.

19. An implantable medical pump system, comprising:
   a blood pump comprising a pump housing defining a passage therethrough and a rotor within the passage, the pump housing at least partially containing one or more elements configured to actuate the rotor to drive fluid through the passage, the pump housing comprising at least one coupling feature;
   a first inflow cannula defining a lumen therethrough and configured to be reversibly attached to the at least one coupling feature, wherein the first inflow cannula comprises a first region along the lumen having a textured blood-contacting surface; and
   a second inflow cannula defining a lumen therethrough having a substantially equivalent flow geometry as the lumen of the first inflow cannula, wherein the second inflow cannula comprises a smooth surface in a second region corresponding to the first region.

20. The implantable medical pump system of claim 12, wherein each of the first and second inflow cannulas is configured to extend into the passage of the pump housing to a rotor well defined by the passage when mechanically coupled to the at least one coupling feature, and the textured blood-contacting surface of the first inflow cannula is disposed along the entire blood flow path to the rotor well.

* * * * *